(12) United States Patent
Kassab et al.

(10) Patent No.: US 10,695,199 B2
(45) Date of Patent: *Jun. 30, 2020

(54) STROKE PREVENTION DEVICES, SYSTEMS, AND METHODS

(71) Applicant: CVDevices, LLC, San Diego, CA (US)

(72) Inventors: Ghassan S. Kassab, La Jolla, CA (US); Hyo Won Choi, San Diego, CA (US); Jose A. Navia, Sr., Buenos Aires (AR)

(73) Assignee: CVDevices, LLC, San Diego, CA (US)

( * ) Notice: Subject to any disclaimer, the term of this patent is extended or adjusted under 35 U.S.C. 154(b) by 337 days.

This patent is subject to a terminal disclaimer.

(21) Appl. No.: 15/584,469

(22) Filed: May 2, 2017

(65) Prior Publication Data

US 2017/0246016 A1 Aug. 31, 2017

Related U.S. Application Data

(63) Continuation-in-part of application No. 15/377,103, filed on Dec. 13, 2016, and a continuation of
(Continued)

(51) Int. Cl.
*A61F 2/86* (2013.01)
*A61F 2/966* (2013.01)
(Continued)

(52) U.S. Cl.
CPC ............... *A61F 2/86* (2013.01); *A61F 2/01* (2013.01); *A61F 2/966* (2013.01); *A61F 2/82* (2013.01);
(Continued)

(58) Field of Classification Search
CPC ...... A61F 2/01; A61F 2/82; A61F 2/86; A61F 2/90; A61F 2/966; A61F 2002/821; A61F 2230/0067; A61F 2250/0039
See application file for complete search history.

(56) References Cited

U.S. PATENT DOCUMENTS

| | | |
|---|---|---|
| 5,332,402 A | 7/1994 | Teitelbaum |
| 5,868,777 A | 2/1999 | Lam |

(Continued)

FOREIGN PATENT DOCUMENTS

JP 1221155 9/1989

OTHER PUBLICATIONS

International Searching Authority, International Search Report, dated Jun. 15, 2010 (PCT/US10/31475).
(Continued)

*Primary Examiner* — Robert A Lynch
(74) *Attorney, Agent, or Firm* — Reichel Stohry Dean LLP; Mark C. Reichel; Natalie J. Dean

(57) ABSTRACT

Deflection devices, systems, and methods for the prevention of stroke. Devices hereof comprise an extension portion and an anchor portion, both of which are configured to prevent the device from advancing into the artery extending from the aortic arch in which the device may be positioned. Additionally, a retrieval system is provided, the system comprising a sleeve catheter and a retrieval device slidably disposed therein. The distal end of the retrieval device comprises one or more attachment portions configured to engage at least a portion of the anchor portion of a device positioned within an artery extending from the aortic arch.

19 Claims, 16 Drawing Sheets

Related U.S. Application Data application No. 14/546,601, filed on Nov. 18, 2014, now Pat. No. 9,636,204, said application No. 15/377,103 is a continuation of application No. 13/264,508, filed as application No. PCT/US2010/031475 on Apr. 16, 2010, now Pat. No. 9,517,148.

(60) Provisional application No. 61/905,509, filed on Nov. 18, 2013, provisional application No. 61/169,767, filed on Apr. 16, 2009.

(51) Int. Cl.
    *A61F 2/01*     (2006.01)
    *A61F 2/90*     (2013.01)
    *A61F 2/82*     (2013.01)

(52) U.S. Cl.
    CPC ........... *A61F 2/90* (2013.01); *A61F 2002/011* (2013.01); *A61F 2002/016* (2013.01); *A61F 2002/821* (2013.01); *A61F 2230/0067* (2013.01); *A61F 2230/0069* (2013.01); *A61F 2230/0078* (2013.01); *A61F 2250/0039* (2013.01); *A61F 2250/0098* (2013.01)

(56) References Cited

U.S. PATENT DOCUMENTS

| | | | |
|---|---|---|---|
| 5,935,139 | A | 8/1999 | Bates |
| 5,944,738 | A | 8/1999 | Amplatz et al. |
| 6,096,071 | A | 8/2000 | Yadav |
| 6,309,399 | B1 | 10/2001 | Barbut et al. |
| 6,361,545 | B1 | 3/2002 | Macoviak et al. |
| 6,499,487 | B1 | 12/2002 | McKenzie et al. |
| 6,682,543 | B2 | 1/2004 | Barbut et al. |
| 6,695,858 | B1 | 2/2004 | Dubrul et al. |
| 6,740,112 | B2 | 5/2004 | Yodfat et al. |
| 7,244,267 | B2 | 7/2007 | Huter et al. |
| 7,367,985 | B2 | 5/2008 | Mazzocchi et al. |
| 7,455,688 | B2 | 11/2008 | Furst et al. |
| 7,479,153 | B2 | 1/2009 | Beief |
| 7,493,162 | B2 | 2/2009 | Girouard et al. |
| 7,537,600 | B2 | 5/2009 | Eskuri |
| 9,636,204 | B2 * | 5/2017 | Kassab ..................... A61F 2/86 |
| 2003/0158574 | A1 | 8/2003 | Esch et al. |
| 2004/0064092 | A1 | 4/2004 | Tsugita et al. |
| 2004/0167613 | A1 * | 8/2004 | Yodfat ..................... A61F 2/01 |
| | | | 623/1.15 |
| 2005/0159773 | A1 | 7/2005 | Broome et al. |
| 2005/0267516 | A1 | 12/2005 | Soleimani et al. |
| 2006/0015138 | A1 | 1/2006 | Gertner |
| 2007/0179592 | A1 | 8/2007 | Schaeffer |
| 2007/0208410 | A1 | 9/2007 | Berra et al. |
| 2008/0140110 | A1 | 6/2008 | Spence |
| 2008/0255603 | A1 | 10/2008 | Naor et al. |
| 2009/0099647 | A1 | 4/2009 | Glimsdale et al. |
| 2009/0254172 | A1 | 10/2009 | Grewe |
| 2012/0041471 | A1 | 2/2012 | Kassab et al. |
| 2013/0131714 | A1 | 5/2013 | Wang |

OTHER PUBLICATIONS

International Searching Authority, Written Opinion of the International Searching Authority, dated Jun. 15, 2010 (PCT/US10/31475).

* cited by examiner

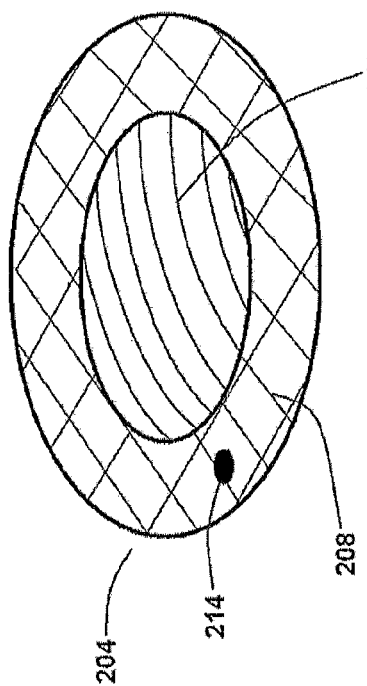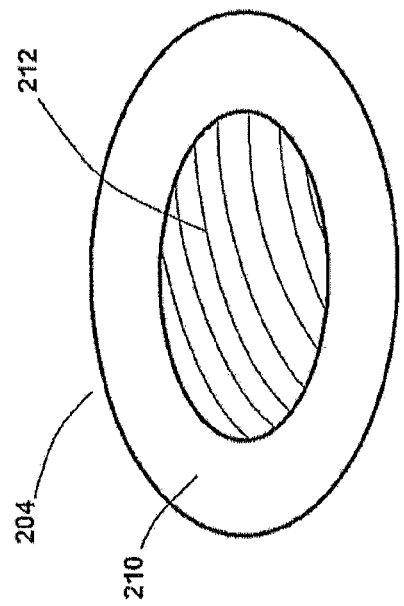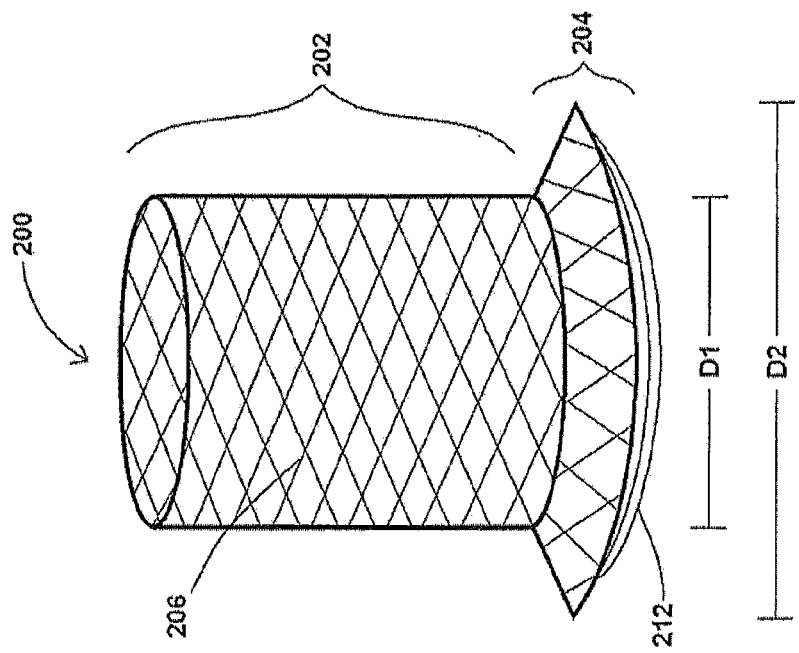

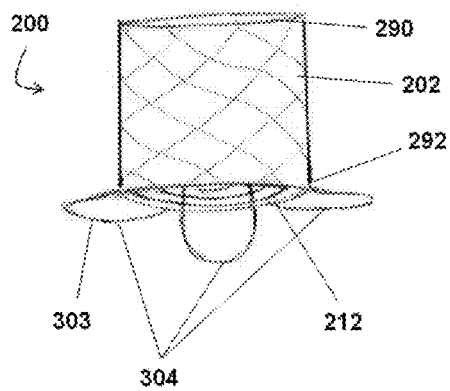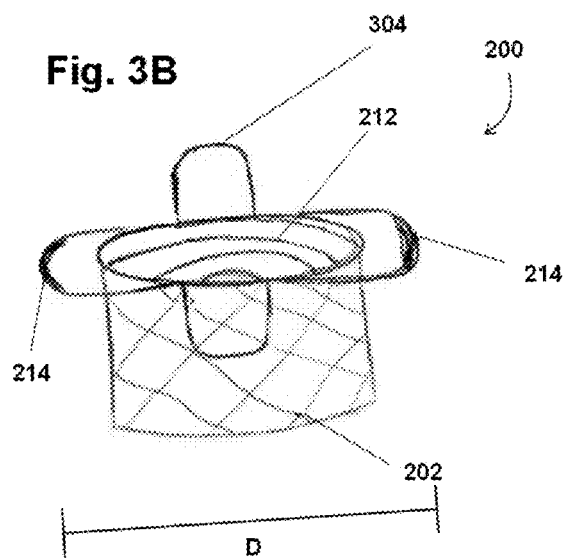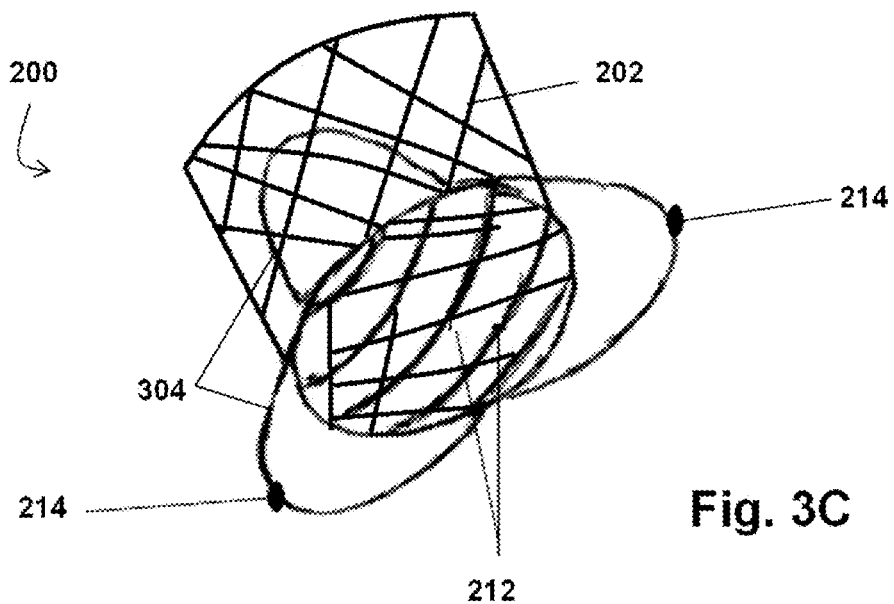

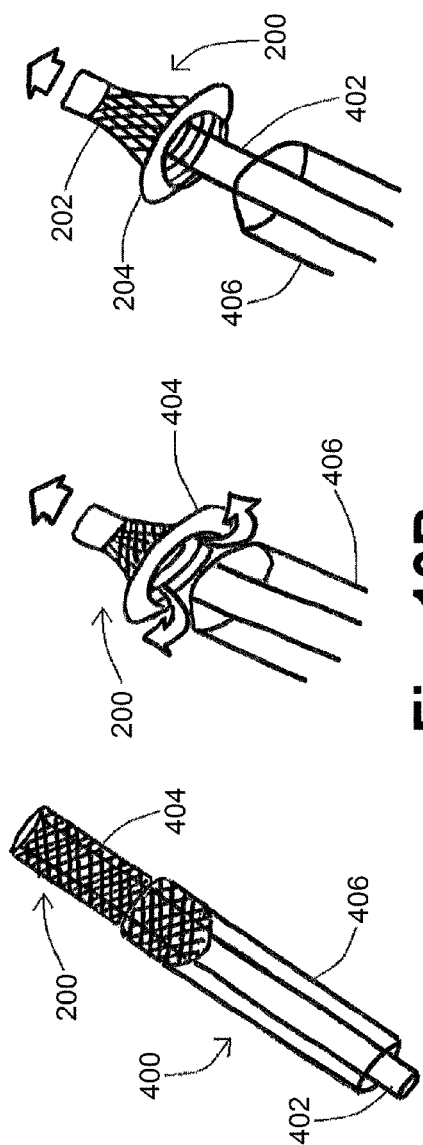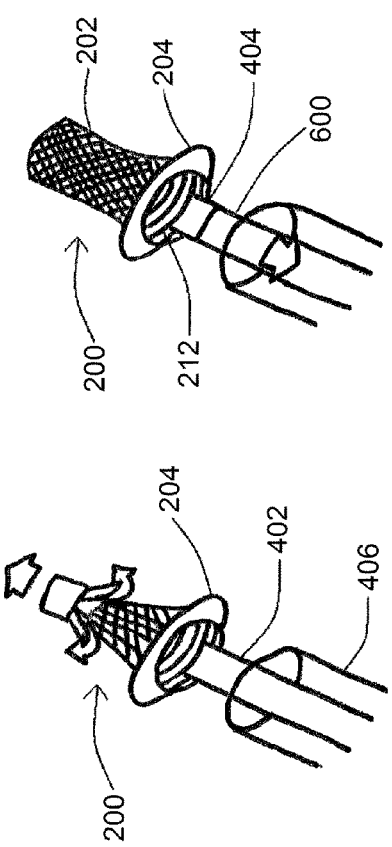

STROKE PREVENTION DEVICES, SYSTEMS, AND METHODS

PRIORITY

This application (a) is related to, and claims the priority benefit of, U.S. patent application Ser. No. 14/546,601, filed Nov. 18, 2014 and issued as U.S. Pat. No. 9,636,204 on May 2, 2017, which is related to, and claims the priority benefit of, U.S. Provisional Patent Application Ser. No. 61/905,509, filed Nov. 18, 2013, and (b) is related to, claims the priority benefit of, and is a U.S. continuation-in-part application of, U.S. patent application Ser. No. 15/377,103, filed Dec. 13, 2016, which is related to, claims the priority benefit of, and is a U.S. continuation application of, U.S. patent application Ser. No. 13/264,508, filed Oct. 14, 2011 and issued as U.S. Pat. No. 9,517,148 on Dec. 13, 2016, which is related to, and claims the priority benefit of, International Application Serial No. PCT/US10/31475, filed Apr. 16, 2010, which is related to, and claims the priority benefit of, U.S. Provisional Patent Application Ser. No. 61/169,767, filed Apr. 16, 2009. The entire contents of the aforementioned priority and related applications are hereby incorporated by reference in their entirety into this disclosure.

BACKGROUND

Stroke

A stroke is defined as a rapidly developing loss of brain function due to a disturbance in the blood supply to the brain. This can be due to ischemia (lack of blood supply) caused by thrombosis or embolism or due to a hemorrhage. As a result, the affected area of the brain is unable to function, leading to the inability to move one or more limbs on one side of the body, the inability to understand or formulate speech, or the inability to see one side of the visual field amongst others.

Each year, about 800,000 people experience a new or recurrent stroke. Approximately 600,000 of these are first attacks, and 200,000 are recurrent attacks. In addition, and on average, someone in the U.S. has a stroke every 40 seconds, and each year, about 55,000 more women than men have a stroke. On average, every 3-4 minutes, someone dies of a stroke. Because women live longer than men, more women than men die of stroke each year. Women accounted for 60.6% of U.S. stroke deaths in 2005. Men stroke incidence rates are greater than women at younger ages but not at older ages. Despite advances in stroke prevention treatments, the incidence of hospitalized stroke and case fatality did not decrease. African-Americans have almost twice the risk of first-ever stroke than whites. The age adjusted stroke incidence rates in people 45-84 years of age are 6.6 per 1000 population in black men, 3.6 in white men, 4.9 in black women, and 2.3 in white women.

Of all strokes, 87% are ischemic, 10% are intracerebral hemorrhage, and 3% are subarachnoid hemorrhage strokes. Stroke accounted for about 1 out of every 17 deaths in the U.S. in 2005, and approximately 53% of stroke deaths in 2005 occurred out of the hospital.

Total stroke mortality in 2005 was about 150,000. The 2005 overall death rate for stroke was 46.6 per 100,000. Death rates were 44.7 for white males, 70.5 for black males, 44.0 for white females, and 60.7 for black females, all per 100,000. When considered separately from other cardiovascular diseases, stroke ranks no. 3 among all causes of death, behind heart disease and cancer.

A report released by the Centers for Disease Control (CDC) in collaboration with the Centers for Medicare and Medicaid Services (CMS), the Atlas of Stroke Hospitalizations Among Medicare Beneficiaries, found that in Medicare beneficiaries, 30-day mortality rate varied by age: 9% in patients 65 to 74 years of age, 13.1% in those 74 to 84 years of age, and 23% in those 85 years of age.

Atrial Fibrillation

Atrial fibrillation (AF) is a significant, independent risk factor for ischemic stroke, increasing risk about 5-fold. The percentage of strokes attributable to AF increases steeply from 1.5% at 50 to 59 years of age to 23.5% at 80 to 89 years of age. Most strokes in patients with AF are cardioembolic caused by embolism of left atrial appendage thrombi, but some are caused by coexisting intrinsic cerebrovascular diseases in typically elderly, often hypertensive patients.

AF carries an annual risk of thromboembolic complications of 3-6%, which is 5-7 times greater than that of controls with sinus rhythm. AF is present in 15-21% of patients affected by stroke. AF/flutter, a strong risk factor for stroke, is arguably the most important finding on cardiac workup in patients with ischemic stroke. Once identified, introduction of oral anticoagulant therapy (warfarin, for example) provides a 40% risk reduction in recurrent stroke compared with antiplatelet therapy. Ischemic stroke with AF is associated with greater disability and mortality than those without AF. However, not all patients can receive anticoagulant or antiplatelet therapies, and the same or other patients may be prone to clots that form in the left atrial appendage and enter the bloodstream, so other types of therapies would be required.

Patients with AF have an increased risk of major, disabling stroke, often caused by large infarctions in the middle cerebral artery territory. Some studies showed that AF was associated with an increased risk of death in the first four weeks after stroke likely due to the advanced age in stroke patients with AF, large infarction, severe neurological deficits, and poor functional outcomes.

First, strokes in patients with AF may largely be cardioembolic, which causes a sudden occlusion of large cerebral arteries without sufficient collateral blood flow, resulting in more severe strokes. Several studies have reported that stroke patients with AF often have large cortical infarcts on computed tomography, and less frequently have lacunar infarction as compared with patients without AF.

Heart Failure

Patients with heart failure (HF) are at increased risk for thromboembolic events. Left ventricular (LV) thrombus provides a substrate for events and a rationale for anticoagulation. Echocardiography studies have yielded conflicting results, however, regarding thrombus prevalence. Among populations with similar degrees of systolic dysfunction, studies have reported over a 20-fold difference in prevalence, ranging from 2.1% to 50%. Moreover, when thrombus is identified, conflicting findings have been reported concerning the risk of future embolic events.

The impact of nonrheumatic atrial fibrillation, hypertension, coronary heart disease, and cardiac failure on stroke incidence was examined in the Framingham Study. Compared with subjects free of these conditions, the age-adjusted incidence of stroke was more than doubled in the presence of coronary heart disease and more than tripled in the presence of hypertension. There was a more than fourfold excess of stroke in subjects with HF and nearly fivefold increase when atrial fibrillation was present. In persons with coronary heart disease or HF, atrial fibrillation doubled the stroke risk in men and tripled the risk in women. Factors that predispose to thromboembolic events in patients with HF include low cardiac output, with relative stasis of blood in dilated cardiac chambers, poor contractility and regional wall motion abnormalities and concomitant atrial fibrillation.

BRIEF SUMMARY

In at least one exemplary embodiment of a device for the prevention of stroke of the present disclosure, the device comprises an extension portion, an anchor portion, and two or more parallel, convex struts. The extension portion has a first end and a second end and is sized and shaped to fit within an artery extending from an aortic arch. The anchor portion comprises a plurality of wings and is coupled with the second end of the extension portion and sized and shaped to prevent the device from advancing into the artery extending from the aortic arch in which the first end of the extension portion may be positioned. In at least one embodiment, the anchor portion comprises a flange configuration. Alternatively, the anchor portion may comprise two or more wings.

The two or more parallel convex struts of the device are positioned across an opening defined within the second end of the extension portion, the two or more parallel convex struts configured to divert an embolus from entering the artery when the first end of the extension portion is positioned within the artery. In another embodiment, the two or more parallel convex struts comprise four or more parallel convex struts. In an exemplary embodiment, when the device is positioned within the artery extending from an aortic arch, the two or more parallel convex struts are positioned either approximately perpendicular to, in a direction of (i.e. approximately parallel with), or in an oblique manner relative to, blood flow within the aortic arch. In an additional embodiment, the device comprises a stent. In yet an additional embodiment, the anchor portion is autoexpandable from a collapsed configuration to an expanded configuration.

In at least one exemplary embodiment of a device for the prevention of stroke of the present disclosure, the extension portion comprises a substantially cylindrical shape. In another embodiment, the extension portion comprises an extension mesh comprising multiple wires. In yet another embodiment, the extension portion has a length between about 1.5 cm to about 2.5 cm. In an additional embodiment, the extension portion has a diameter between about 6 mm to about 8 mm when the extension portion is in an expanded configuration. In yet an additional embodiment, the extension portion has a diameter between about 1.8 mm to about 2.0 mm when the extension portion is in a compressed configuration.

In at least one exemplary embodiment of a device for the prevention of stroke of the present disclosure, the device is comprised of a material selected from the group consisting of stainless steel, cobalt-chromium-nickel-molybdenum-iron alloy, tantalum, nitinol, nickel-titanium, polymer materials, and a shape-memory polymer.

In at least one exemplary embodiment of a device for the prevention of stroke of the present disclosure, the device further comprises one or more radiopaque markers positioned upon at least one of the anchor portion, such as at one or more of the plurality of wings. In an additional embodiment, the one or more radiopaque markers are positioned relative to the two or more parallel convex struts. In yet additional embodiments, when the first end of the extension portion is positioned within the artery extending from an aortic arch, the one or more radiopaque markers facilitate alignment of the device so that the two or more parallel convex struts are positioned either approximately perpendicular to, or in a direction of (i.e. approximately parallel with), or in an oblique manner relative to, blood flow within the aortic arch. In at least one exemplary embodiment of a device for the prevention of stroke of the present disclosure, the diameter of each of the two or more parallel convex struts is between about 0.25 mm and about 1.0 mm, inclusive. In another embodiment, the two or more parallel convex struts are positioned between about 0.75 mm to about 1.0 mm, inclusive, from one another. In yet another embodiment, the two or more parallel convex struts are flexible. In various embodiments, each wing of the plurality of wings comprises a wire forming a loop relative to the second end of the extension portion. In at least one embodiment, the extension portion comprises a stent frame without an extension mesh coupled thereto or formed therein. In various embodiments, the stent frame comprises a plurality of extension struts connected to one another by way of one or more connection struts.

In at least one exemplary embodiment of a retrieval system for the prevention of stroke of the present disclosure, the system comprises at least one device for the prevention of stroke, a sleeve catheter and a retrieval device. The at least one device comprises an extension portion having a first end and a second end (the extension portion sized and shaped to fit within an artery extending from an aortic arch), an anchor portion comprising a plurality of wings and coupled with the second end of the extension portion (the anchor portion sized and shaped to prevent the device from advancing into the artery extending from the aortic arch in which the first end of the extension portion may be positioned), and two or more parallel convex struts positioned across an opening defined within the second end of the extension portion, the two or more parallel convex struts configured to divert an embolus from entering the artery when the first end of the extension portion is positioned within the artery. The sleeve catheter is configured for intravascular insertion and advancement, the sleeve catheter comprising a proximal end, an open distal end, and a lumen extending therebetween, and the retrieval device slidably disposed within the lumen of the sleeve catheter, the retrieval device comprising a proximal end for manipulation by a user and a distal end comprising one or more second attachment portions, wherein each of the one or more second attachment portions of the retrieval device are configured to engage the first attachment portion of the anchor portion of the device. In another embodiment, the system further comprises a conical dilator sized and shaped to slidingly engage the hypotube. In yet another embodiment, the conical dilator comprises a tapered distal and a proximal end. In an additional embodiment, the folder has an inner diameter, and wherein the tapered distal end of the conical dilator is sized and shaped to fit within the inner diameter of the folder. In yet an additional embodiment, when the device is positioned within the artery extending from an aortic arch, the two or more parallel convex struts either approximately perpendicular to, in a direction of (i.e. approximately parallel with), or in an oblique manner relative to, blood flow within the aortic arch. In another embodiment, the retrieval device of the system comprises one or more wires. In yet other embodiments, the system comprises two devices for prevention of a stroke. Furthermore, in at least one embodiment, the first attachment portion of the anchor portion comprises a screw tip and a first magnet and the second attachment portion of the retrieval device comprises a screw hole and a second magnet, and the screw tip and the first magnet of the first attachment portion are configured to securely engage with the screw hole and the second magnet of the second attachment portion, respectively. Additionally, in other embodiments, the second attachment portion of the retrieval device comprises a lace component and the first attachment portion of the anchor portion comprises a hook tip configured to engage the lace component of the retrieval device.

In at least one exemplary embodiment of a method for preventing stroke of the present disclosure, the method comprises the steps of introducing a device for preventing stroke into a body, navigating the device within the body until the device reaches an aortic arch, and positioning the device within a first vessel branching from the aortic arch so that the two or more convex struts are positioned either approximately perpendicular to, or in a direction of (i.e. approximately parallel with), or in an oblique manner relative to, blood flow within the aortic arch. In another embodiment, in the step of introducing a device for preventing stroke into a body, the device comprises an extension portion having a first end and a second end, an anchor portion comprising a plurality of wings and coupled with the second end of the extension portion and sized and shaped to prevent the device from advancing into the artery extending from the aortic arch in which the first end of the extension portion may be positioned, and two or more convex struts positioned across an opening defined within the second end of the extension portion. Here, the extension portion may be sized and shaped to fit within an artery extending from the aortic arch and/or the two or more convex struts of the device may be configured to divert an embolus from entering the artery when the first end of the extension portion is positioned within the artery. In yet another embodiment, the step of positioning the device is performed by aligning the device within the vessel by detecting one or more radiopaque markers positioned upon the device. Furthermore, placement of the device within the first vessel does not significantly affect upstream blood flow patterns. In an additional embodiment, the step of positioning the device comprises positioning the device within an innominate artery.

In at least one exemplary embodiment of a method for preventing stroke of the present disclosure, the method further comprises the steps of introducing a second device for preventing stroke into the body; navigating the second device within the body until the second device reaches the aortic arch; and positioning the second device within a second vessel branching from the aortic arch. In this manner, two or more convex struts of the second stent are positioned either approximately perpendicular to, in a direction of (i.e. approximately parallel with), or in an oblique manner relative to, blood flow within the aortic arch. In another embodiment, the step of positioning the second device comprises positioning the second device within a common carotid artery. In yet another embodiment, the step of positioning the first device comprises positioning the first device within an innominate artery, wherein the first device is capable of diverting an embolus from entering the innominate artery and the second device is capable of diverting the embolus from entering the common carotid artery.

In at least one exemplary embodiment of a method for preventing stroke of the present disclosure, the method further comprises the step of anchoring the device within the first vessel by deploying the extension portion and the anchor portion of the device. Additionally, the step of anchoring the device within the first vessel may further comprise moving the extension portion from a collapsed position to an expanded position and moving the anchor portion from a collapsed position to an expanded position. In yet another exemplary embodiment of the method for preventing stroke of the present disclosure, the method further comprises the steps of retrieving the stent from the first vessel and removing the stent from the body. In an additional embodiment, the steps of retrieving the stent from within the first vessel and removing the stent from the body further comprise the steps of: introducing a retrieval system into the body, navigating the sleeve catheter within the body until the open distal end of the sleeve catheter reaches an aortic arch, advancing the distal end of the retrieval catheter through the open distal end of the sleeve catheter so that the one or more attachment portions engage the anchor portion of the device, disengaging the device from the first vessel, and withdrawing the device and the retrieval system from the body. In yet another embodiment of the method, the step of introducing a retrieval system into the body further comprises the retrieval system comprising a sleeve catheter configured for intravascular insertion and advancement, the sleeve catheter comprising a proximal end, an open distal end, and a lumen extending therebetween, and a retrieval device slidably disposed within the lumen of the sleeve catheter, the retrieval device comprising a proximal end for manipulation by a user and a distal end comprising one or more attachment portions, each of which are configured to engage the anchor portion of the device.

BRIEF DESCRIPTION OF THE DRAWINGS

FIGS. 2A and 2B show exemplary embodiments of a device for the prevention of stroke, according to the present disclosure;

FIG. 2C shows an embodiment of a device comprising a planar flange, according to the present disclosure;

FIGS. 3A and 3B show side views of an embodiment of a device comprising two or more wings, according to the present disclosure;

FIG. 3C shows an interior view of the device of FIGS. 3A and 3B;

FIGS. 10A-10E show various steps of a method for positioning a device within a body, according to the present disclosure;

Figure 1:
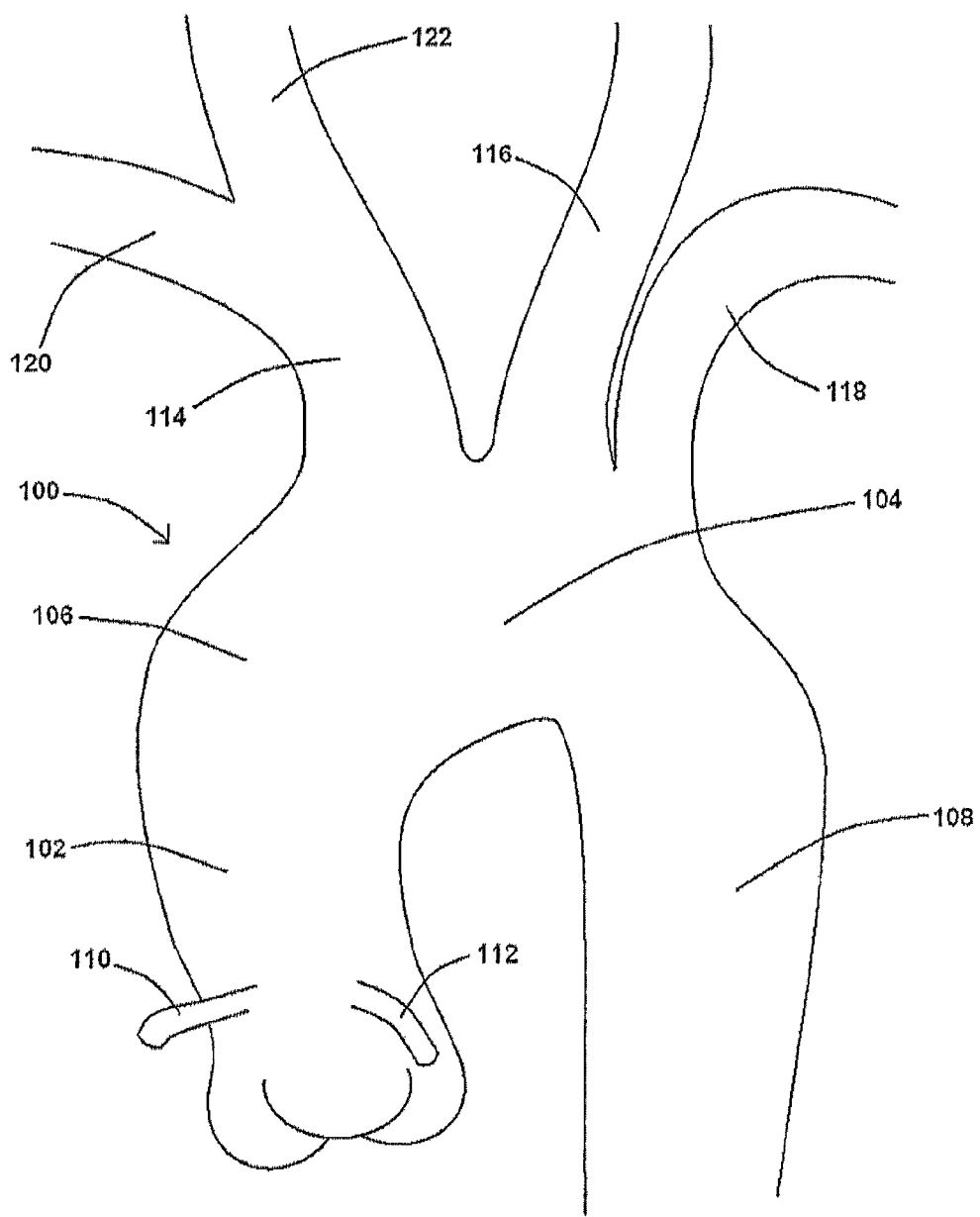
FIG. 1 shows a diagram of at least a portion of an aorta, according to the present disclosure.

An overview of the features, functions and/or configurations of the components depicted in the various figures will now be presented. It should be appreciated that not all of the features of the components of the figures are necessarily described. Some of these non-discussed features, such as various couplers, etc., as well as other discussed features, are inherent from the figures themselves. Other non-discussed features may be inherent in component geometry and/or configuration.

DETAILED DESCRIPTION

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended. Furthermore, numerous specific details are set forth in order to provide a thorough understanding of the present disclosure. Particular examples may be implemented without some or all of these specific details. In other instances, well known devices or processes have not been described in detail so as to not unnecessarily obscure the present disclosure.

Various systems, methods and techniques of the present disclosure will sometimes describe a connection between two components. Words such as attached, affixed, coupled, connected, and similar terms with their inflectional morphemes are used interchangeably, unless the difference is noted or made otherwise clear from the context. These words and expressions do not necessarily signify direct connections, but include connections through mediate components and devices. It should be noted that a connection between two components does not necessarily mean a direct, unimpeded connection, as a variety of other components may reside between the two components of note. Consequently, a connection does not necessarily mean a direct, unimpeded connection unless otherwise noted. Furthermore, wherever feasible and convenient, like reference numerals are used in the figures and the description to refer to the same or like parts or steps. Additionally, the drawings are in a simplified form and not to precise scale.

The disclosure of the present application provides various devices, systems, and methods for the prevention of stroke. The devices, systems, and methods disclosed herein facilitate stroke prevention, in part, by addressing specific areas of the heart and diverting the trajectories of blood clots away therefrom with minimal to no influence on resistance of blood flow through such areas and/or significantly affect upstream blood flow patterns.

A diagram of at least a portion of an exemplary aorta is shown in FIG. 1. An aorta 100 is the main trunk of a vascular system which conveys oxygenated blood to the tissues of a body. It begins at the upper part of the left ventricle, where it may be approximately 3 cm in diameter in an adult human. As shown in FIG. 1, and at the union of the ascending aorta 102 with the aortic arch 104 (or the "arch of aorta"), the caliber of the vessel is increased, owing to a bulging of its right wall. This dilatation is termed the aortic bulb 106 (or bulb of the aorta), and on transverse section shows a somewhat oval figure. The ascending aorta 102 is contained within the pericardium and is enclosed in a tube of the serous pericardium. It ascends for a short distance (the ascending aorta 102 is about 5 cm in length in an adult human), arches backward, and then descends within the thorax and abdomen (the descending aorta 108) and ends into the right and left common iliac arteries (about 1.7 cm in diameter in an adult human). The right coronary 110 and the left coronary 112, as shown in FIG. 1, branch from the ascending aorta 102.

There are three arteries that branch from the aortic arch 104, namely the innominate artery 114, the left common carotid artery 116, and the left subclavian artery 118. Instead of arising from the highest part of the aortic arch 104, these branches may spring from the commencement of the aortic arch 104 or the upper part of the ascending aorta 102. The distance between the aortic arch 104 or the upper part of the ascending aorta 102 at their origins may be increased or diminished, the most frequent variation being the approximation of the left common carotid artery 116 toward the innominate artery 114. In addition, and as shown in FIG. 1, the innominate artery 114 branches into the right subclavian artery 120 and the right common carotid artery 122.

Ischemic strokes, the most common type of stroke, occur when blood clots or other debris are swept through the bloodstream and lodge in one or more of the aortic branches 114, 116. As the innominate and left common carotid arteries 114, 116 ultimately supply blood to the brain, the partial or complete blockage thereof reduces or inhibits blood flow to the brain, thus increasing the risk of ischemic stroke. Ejection dynamics of blood clots from the left ventricle is diverse and random, with clots having different release velocities at different stages of the cardiac cycle. Furthermore, blood clots can vary in size—typically in the range of about 2 mm to about 6 mm—which can also have a significant effect on clot velocity and their flow patterns as they leave the heart. In addition, the hemodynamics in the aortic arch 104 are typically characterized as complex flow patterns due to the arch curvature and branches 114, 116. Accordingly, clot trajectory is a complex function of aortic flow conditions, discrete phase behavior of clots, and their dynamic interactions. To prevent ischemic stroke, not only must clots be prevented from lodging within the aortic branches 114, 116, but the solution must be mindful of the complexity of the aortic flow field and not generate a substantial resistance to flow therethrough.

The devices, systems, and methods of the present application are configured to maintain a balance between efficacy in deflecting blood clots from an artery extending from the aortic arch 104 and affecting minimal influence on resistance to blood flow therethrough. In this manner, such deflection devices, systems and methods can ensure diversion of blood clots away from the aortic branches 114, 116, rather than blocking clots on the device and thereby obstructing the underlying arteries. FIGS. 2A-2C show exemplary embodiments of a device of the present application for the prevention of stroke. In application, such device (and any embodiments thereof) may be used with one or more of the aortic branches 114, 116, 118 to deflect the trajectory of blood clots destined for the structures of the aorta 100 with negligible change in blood flow resistance. As shown in FIG. 2A, an exemplary device 200 may comprise a stent comprising an extension portion 202 and a flange portion 204. Extension portion 202, as shown in FIG. 2A, may comprise a cylindrical stent sized and shaped to fit securely within an aortic branch. An exemplary extension portion 202 may comprise, for example, extension mesh 206 comprising multiple wires as shown in FIG. 2A. Flange portion 204 may comprise an inner diameter (shown as D1 in FIG. 2A) and an outer diameter (shown as D2), whereby D2 is larger than D1. In at least one embodiment, device 200 is collapsible, similar to a traditional stent. Alternatively or additionally, the device 200 (or independent components thereof) may be autoexpandable to facilitate secure anchoring within an artery and/or the long term stability of the device 200 after placement.

In at least one embodiment of device 200 of the disclosure of the present application, device 200 comprises an autoexpandable metallic stent comprising a proximal flange (flange portion 204) and a distal cylindrical tube (extension portion 202). In an exemplary embodiment, extension portion 202 is approximately 1.0 cm to 2.5 cm in length. In at least one embodiment of device 200, the diameter of the stent is approximately 6 to 8 mm. Suitable material for a device 200 includes but is not limited to, stainless steel, cobalt-chromium-nickel-molybdenum-iron alloy, tantalum, nitinol, nickel-titanium, polymer materials, and various shape-memory polymers known in the art, including polyurethane, polytetrafluoroethylene or polytetrafluoroethene (PTFE), or another synthetic material.

Flange portion 204, as shown in the exemplary embodiments shown in FIGS. 2A and 2B, comprises flange mesh 208 comprising multiple wires. In another embodiment, and as shown in FIG. 2C, flange portion 204 comprises a planar flange 210 comprised of metal, plastic, or any other material suitable for such a flange portion 204. The flange portion 204 may comprise any length and/or diameter that is effective to impede the progression of the device 200 within an artery when positioned within a body. In at least one embodiment, the flange portion 204 is between about 3 mm and about 5 mm in length. Furthermore, the flange portion 204 may be configured to move between a collapsed position having a smaller diameter for delivery and/or retrieval of the device 200 (see FIG. 6A) and an expanded position having a larger diameter (see FIG. 2A). For example, in at least one embodiment, the flange portion 204 is comprised of an autoexpandable material such that when the flange portion 204 is released from a delivery mechanism, it automatically moves into the expanded position to assist in anchoring the device 200 within an artery of interest. As shown in FIGS. 2A-2C, the device 200 also comprises two or more convex struts 212 operable to divert, for example, an embolus, from entering the inner portion of device 200 (the inner portion defined by extension portion 202) while still allowing blood to flow therethrough without significantly affecting flow resistance. Convex struts 212 are one example of such an embolus diversion portion of device 200, noting that other embodiments of an embolus diversion not comprising convex struts 212 may be useful with device 200. For example, and instead of convex struts 212, an exemplary embolus diversion portion may comprise a mesh (similar to, for example, extension mesh 206 and/or flange mesh 208), whereby such a mesh is operable to divert an embolus from entering the inner portion of device 200.

Convex struts 212, in an exemplary embodiment, are positioned along device 200 to cover the proximal orifice of the cylindrical stent (device 200). In at least one embodiment of a device 200 of the disclosure of the present application, the diameter of each convex strut 212 is approximately 0.25 mm to 1.0 mm, and the distance between each convex strut 212 is approximately 0.75 mm to 1.0 mm. In at least one exemplary embodiment, the diameter of each convex strut 212 is approximately 0.75 mm and the distance between each convex strut 212 is approximately 0.75 mm, which has been found to provide beneficial deflection efficacy with respect to emboli while affecting only negligible change in flow resistance through the underlying artery.

It will be appreciated that the number of convex struts 212 present on the device 200 may be customized according to a user's preferences and/or patient specifications. Furthermore, each convex strut 212 of the device 200 need not be configured identically; indeed, device 200 may be configured to employ various combinations of convex strut 212 diameter, intervals, and heights. Moreover, the convex struts 212 may also comprise varying cross-sectional areas and/or a non-spherical profile of the convex envelope. Convex struts 212 may comprise material the same and/or similar to the material used to prepare other portions of device 200, and may also be a combination of a metal plus polyurethane, polytetrafluoroethylene or polytetrafluoroethene (PTFE), or another synthetic material.

In at least one embodiment, convex struts 212 may be semi-rigid or flexible in order to allow the removal of a hypotube 402 (see FIGS. 6A-7B) and/or allow the passage of a catheter stent device, including device 200, for stenting the carotid artery, for example, if it develops an atherosclerotic plaque. In an exemplary embodiment, the strut shape can be convex or semi-convex in order to be easily and constantly "washed" by the aortic blood flow and therefore avoid local thrombosis. If an embolus lands on a strut, the strut shape will also allow it to wash off to the periphery not only preventing the embolus from entering the brain vascular system, but also deflecting the embolus away from the ostium of the artery to ensure the blood flow therethrough does not become restricted or blocked (i.e. the embolus does not stick to the convex struts 212, but rather deflects off).

In addition, and in the exemplary embodiment shown in FIG. 2B, device 200 may further comprise one or more radiopaque markers 214 located proximally and/or distally on device 200 to aid the placement of device 200 within a body. For example, in at least one embodiment, one or more radiopaque markers 214 are positioned on the flange portion 204 in a location(s) relative to the convex struts 212 of the device 200. Accordingly, when the device 200 is positioned within an artery, the one or more markers 214 on the device 200 can be visualized to identify the orientation of the convex struts 212 relative to the direction of the blood flow.

Now referring to FIGS. 3A-3C, an additional exemplary embodiment of the device 200 is shown. As illustrated in FIG. 3A, in this embodiment, instead of the mesh or planar flange portion 204, the device 200 comprises two or more wings 304 extending from the extension portion 202. In at least one embodiment, each of the wings 304 is defined by a wire 303. As shown in FIG. 3A, for example, each wing 304 (or wire 303 of each wing 304) extends from a second end 292 of extension portion 202, noting that extension portions 202 referenced herein have a first end 290 (as shown in FIG. 3A, for example) configured to extend within a vessel, and a second end 292 at the location of the various struts 212 and/or wings 304. Each wing 304 of the plurality of wings 304, for example, may comprise a wire 303 forming a loop relative to the second end 292 of the extension portion 202. The plane of each wing 304 may be left as an open space (as shown in FIGS. 3A-3C), or covered by a mesh or any other suitable material. When the embodiment of the device 200 having two or more wings 304 is positioned within a body, the wings 304 contact the underlying tissue at intervals, thereby utilizing a minimized structure to hold the device 200 in place as compared to the device 200 comprising the flange portion 204.

Similar to the flange portion 204, wings 304 of the device 200 are sized and configured to impede the progression of the device 200 within an artery when positioned within a body. Additionally, when the device 200 is placed within a proximal opening of the innominate artery 114 or the left common carotid artery 116, the wings 304 may further provide a support structure over the aortic wall of the aortic arch 104 at the entrance of the supra-aortic branches 114, 116. The wings 304 may be between about 3 mm and about 5 mm in length. As shown in FIGS. 3A-3C, wings 304 may comprise a petal configuration; however, it will be noted that any suitable shape or configuration any be employed and that each wing 304 of the device 200 need not have the same length and/or configuration. In addition, in the exemplary embodiment shown in FIG. 3C, the wings 304 of the device 200 may further comprise one or more radiopaque markers 214.

Similar to the flange portion 204, the wings 304 are configured to move between a collapsed position having a smaller overall diameter (see FIG. 6B) and an expanded position having a larger overall diameter D (see FIG. 3B). In at least one embodiment, each of the wings 304 are hingedly coupled with the extension portion 202 and biased to the expanded position. As such, when the wings 304 are not held in the collapsed position, the wings 304 automatically move to the expanded position. As described in further detail herein, movement of the wings 304 between the collapsed and expanded positions facilitates delivery/retrieval and the long term stability of the device 200 within an artery.

Figure 4:
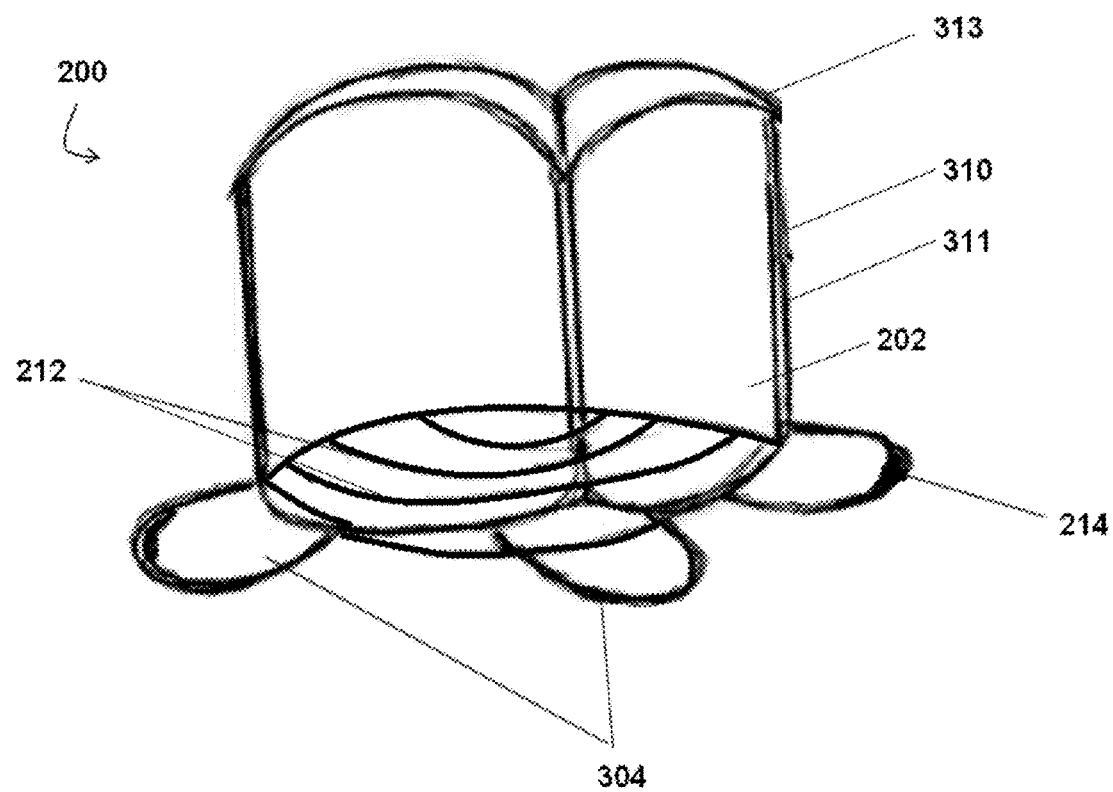
FIG. 4 shows a side view of an embodiment of a device for the prevention of stroke comprising a stent frame according to the present disclosure.

FIG. 4 shows yet another exemplary embodiment of the device 200. As illustrated in FIG. 4, the extension portion 202 of the device 200 may alternatively comprise a stent frame 310 without the inclusion of extension mesh or other materials thereon. In this embodiment of the device 200, the extension portion 202 has significantly less structure than the embodiment shown in FIG. 2A. As with the previously described embodiments, the stent frame 310 may comprise an autoexpandable metallic stent capable of radial expansion such that, when deployed within an artery, the stent frame 310 anchors the device 200 therein by way of radial force. While the embodiment of FIG. 4 comprises wings 304, it will be appreciated that a device 200 comprising the stent frame 310 may alternatively comprise the flange portion 204 or any other component described herein. Exemplary stent frames 310, such as shown in FIG. 4, may comprise a plurality of extension struts 311 positioned around a relative perimeter or circumference of device 200 (such as around the opening where convex struts 212 are located), extending from second end 292 toward first end 290, and may be connected to one another using one or more connection struts 313, which may be curved as desired as shown in FIG. 4.

Figure 5A:
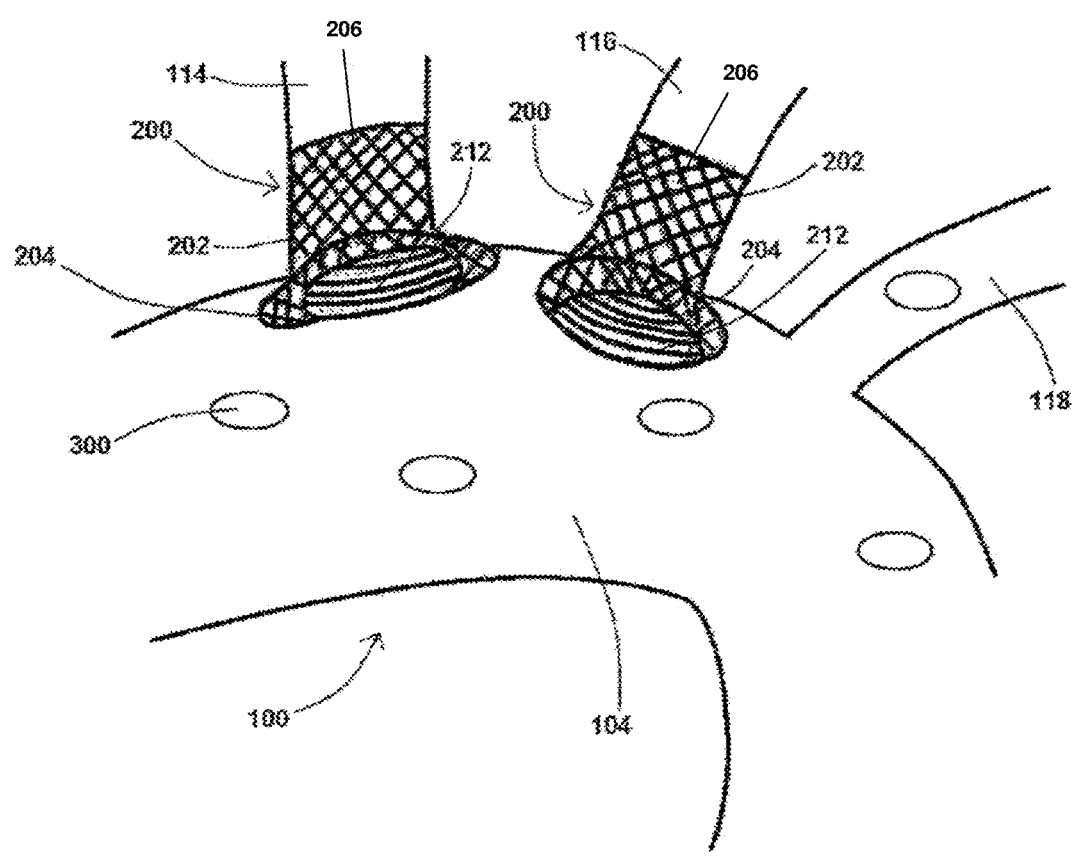
FIG. 5A shows exemplary devices for the prevention of stroke positioned within arteries extending from a portion of an aorta with the convex struts in alignment with blood flow, according to the present disclosure.
Figure 5B:
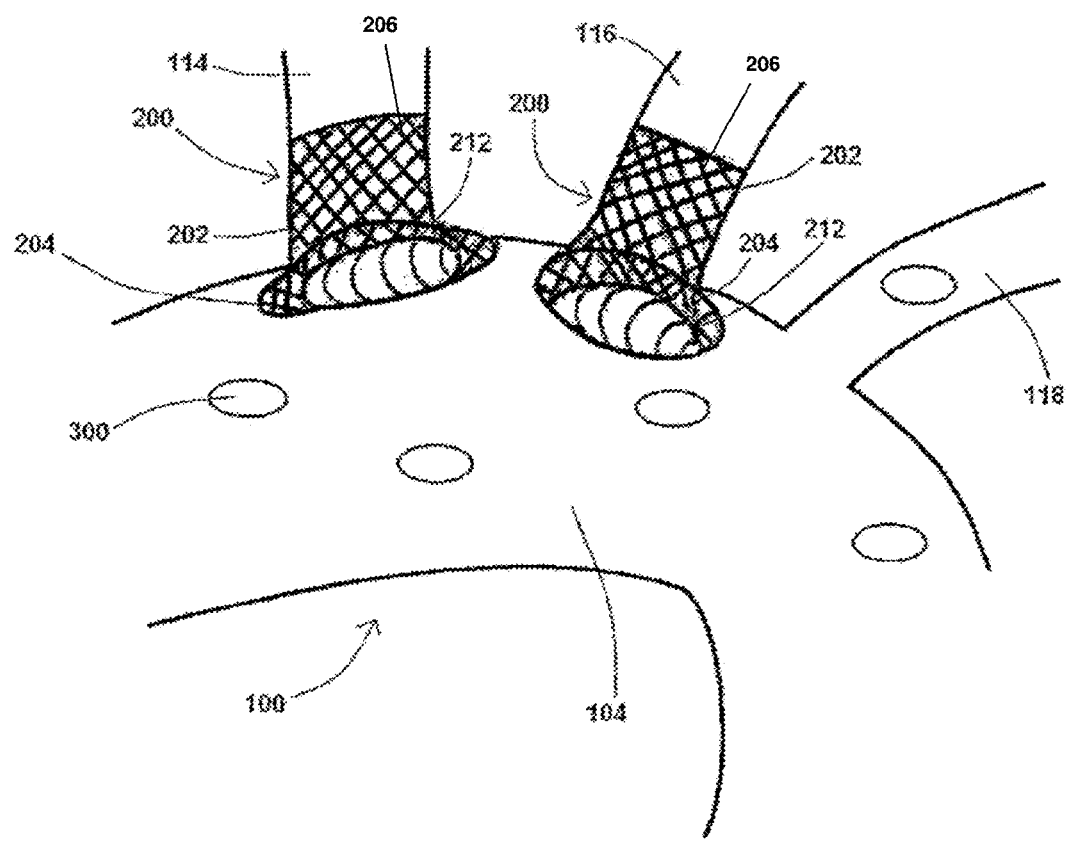
FIG. 5B shows exemplary devices for the prevention of stroke positioned within arteries extending from a portion of an aorta with the convex struts in alignment approximately perpendicular to blood flow, according to the present disclosure.

Exemplary devices for the prevention of stroke positioned within a portion of an aorta are shown in FIGS. 5A and 5B. While the devices 200 illustrated in FIGS. 5A and 5B both comprise a flange portion 204 and an extension portion 202 having extension mesh 206, it will be understood that any embodiments of the device 200 of the present disclosure can be positioned pursuant to and are capable of the same functionality described in connection with FIGS. 5A and 5B.

As shown in FIGS. 5A and 5B, two devices 200 are positioned within arteries branching from aorta 100, with one device 200 positioned partially within innominate artery 114 and another device 200 positioned partially within left common carotid artery 116. Device 200 within innominate artery 114 is positioned such that extension portion 202 is positioned within a portion of innominate artery 114 extending from aortic arch 104 and flange portion 204 prevents device 200 from advancing further into innominate artery 114. Similarly, a device 200 is shown in FIGS. 5A and 5B positioned within left common carotid artery 116 such that extension portion 202 is located within a portion of left common carotid artery 116 extending from aortic arch 104 and flange portion 204 prevents device 200 from advancing further into left common carotid artery 116. In at least one embodiment, flange portion 204 completely covers and exceeds the size of the entrance of the artery in which device 200 is positioned. In an exemplary embodiment of device 200 positioned within an artery as referenced herein, the distal cylindrical portion of the stent (extension portion 202 of device 200) additionally or alternatively anchors device 200 by applying radial force to the arterial walls of the artery in which device 200 is placed. In this manner, both the extension portion 202 and the flange portion 204 may act to anchor the device 200 in place when positioned within an artery.

As shown in the exemplary embodiments of device 200 shown in FIG. 5A, convex struts 212 are aligned in a direction similar to the flow of blood within aorta 100. In such an alignment, and as blood flows through aorta 100, an embolus 300 present within aorta 100 (specifically within the aortic arch 104) would be guided by the blood flow along convex struts 212 and across the proximal opening of the aortic branch. As shown in FIG. 5B, the convex struts 212 of both devices 200 are aligned in a direction approximately perpendicular to the flow of blood within aorta 100. In such an alignment, an embolus 300 present within aorta 100 would contact convex struts 212 and be deflected therefrom with little or no risk of embolus 300 being trapped therein. As referenced herein, convex struts 212 may also be positioned in the direction of (i.e., approximately parallel with), or in an oblique manner relative to, blood flow within the aortic arch 104 as shown in FIG. 5A. In application, the device 200 may be positioned within an artery to achieve any orientation of the convex struts 212 relative to the flow field that may be desired in accordance with patient specifications and/or user preference.

Positioning the devices 200 as shown in FIGS. 5A and 5B prevents an embolus 300 from entering the innominate artery 114 and the left common carotid artery 116, but allows the embolus 300 to enter the left subclavian artery 118. Because the innominate and left common carotid arteries 114, 116 supply blood flow to the brain, in this example, the devices 200 thus prohibit the embolus 300 from advancing to the brain vascular system, thereby significantly reducing a patient's risk of ischemic stroke. Instead, the embolus 300 is allowed to flow into other arteries—such as the femoral or iliac arteries, for example—where such embolus 300 can be filtered from or sucked out of the blood stream using an appropriate medical procedure. In other words, such an arrangement of devices 200 may effectively prevent a patient from having a stroke by deflecting any embolus 300 present in the blood stream away from the vessels that feed the brain and instead routing such emboli 300 to a location where they may be easily and safely removed.

In summary, and as described above with respect to FIGS. 5A and 5B, for example, the present disclosure provides a device 200, which may be referred to as a percutaneous carotid emboli rerouting device, configured for individual delivery to an artery given off by the aortic arch 104 (namely the innominate artery 114, the left common carotid artery 116, and the left subclavian artery 118) to avoid the passage of embolic or thromboembolic material (an embolus 300, which may be, for example, a clot, calcium, etc.) to the brain vascular system. Furthermore, the present disclosure provides for the provision of more than one of these devices 200 to the arteries off the aortic arch 104 such that an arrangement of devices 200 prevents thromboembolic stroke in patients with different cardiovascular diseases from cardiac origin.

At least one goal of the devices, systems, and methods of the present disclosure is to reroute an embolus distally to the arterial system (iliac or femoral arteries) to avoid disabling stroke, decrease mortality and avoid physical impairment with a poor quality of life. As previously mentioned, unlike stroke, medical or surgical treatment of the peripheral arterial embolus (fibrinolitic drugs, surgical embolectomy, or endovascular embolus suction) can be provided with little residual effect. This may be particularly useful to patients who have undergone medical procedures associated with a high risk of stroke and/or blood clots being released following the procedures (e.g, transcatheter aortic valve implantation ("TAVI"), mitral valve replacement, calcific mitral valve insufficiency, balloon dilation, etc.). For example, the general risk of stroke after TAVI is about three percent (3%), which increases to about six to ten percent (6-10%) thirty days following the procedure, and again to about seventeen to twenty-four percent (17-24%) one year following the procedure. As such, while TAVI (or similar procedures) is often used to repair a patient's heart and/or circulatory system, the procedure often results in brain damage due to its side-effect of increasing the occurrence of blood clots.

The devices, systems and methods of the present disclosure can be used in connection with such patients to divert the resulting clots. Moreover, the devices, systems and methods described herein are also particularly applicable to patients who cannot receive anticoagulants, are prone to clots forming in the left atrial appendage and entering the bloodstream, or simply present an elevated risk for brain damage due to stroke. The risk of brain damage can also generally be reduced with the elderly by employing the devices, systems and methods disclosed herein.

Figure 6A:
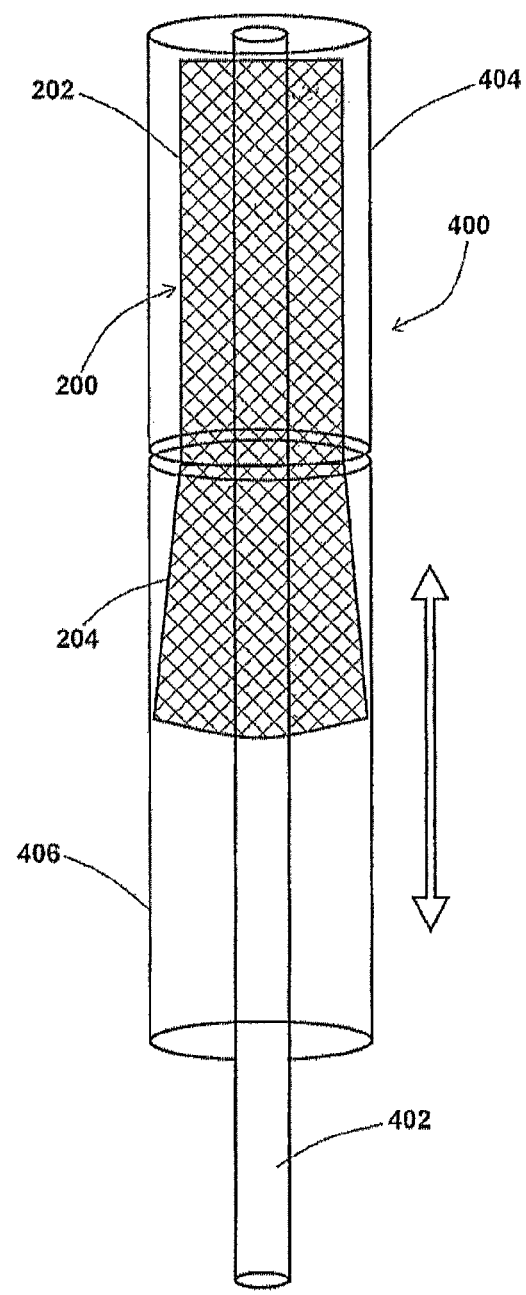
FIG. 6A shows an exemplary embodiment of a system for preventing stroke, according to the present disclosure.
Figure 6B:
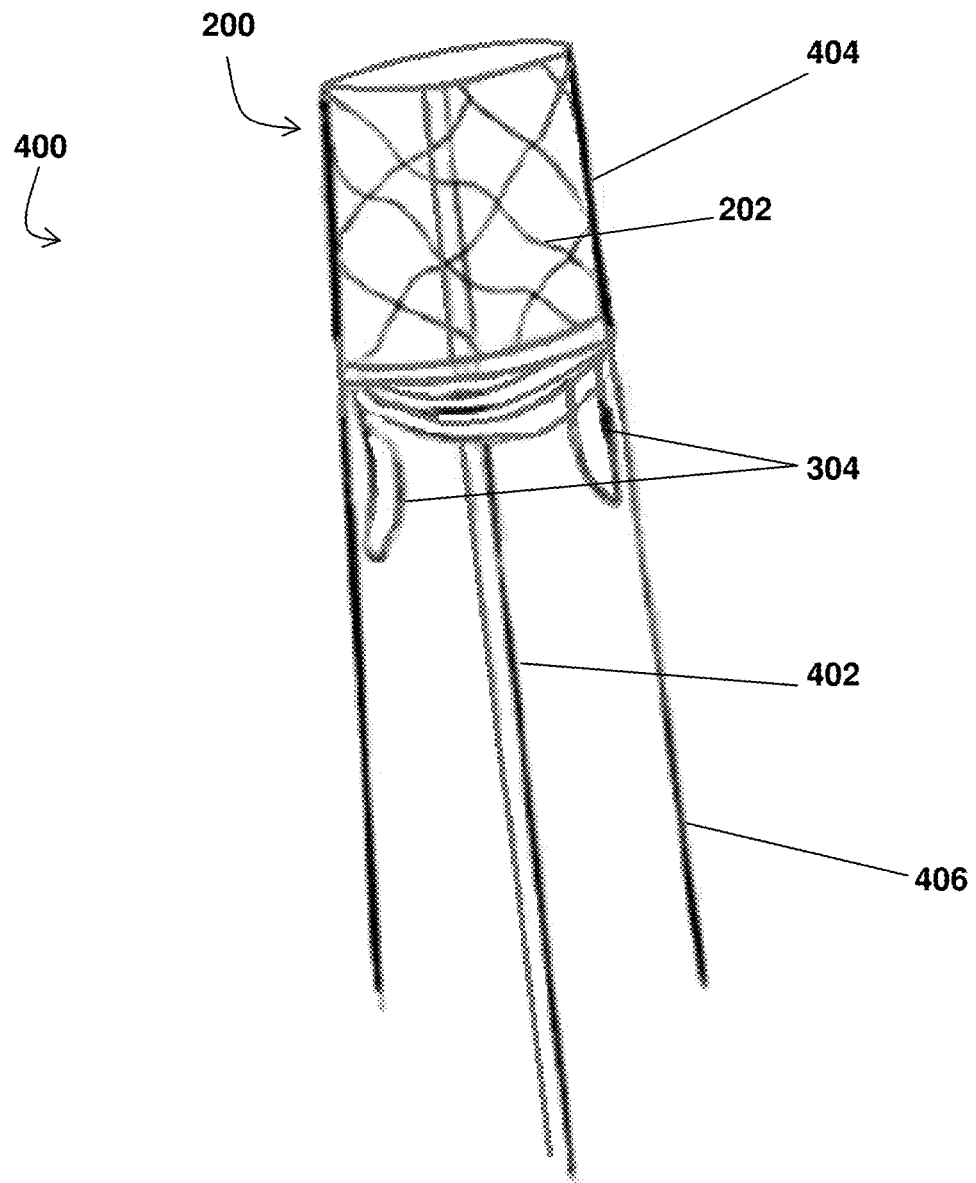
FIG. 6B shows an exemplary embodiment of a system for preventing stroke, the system comprising a device having two or more wings, according to the present disclosure.

Exemplary embodiments of a system for preventing stroke of the present disclosure is shown in FIGS. 6A and 6B. As shown in FIGS. 6A and 6B, system 400 comprises a hypotube 402 having a distal end and a proximal end, and in at least one exemplary embodiment, hypotube 402 comprises a folder 404 coupled to the distal end of hypotube 402. In the embodiment shown in FIG. 6A, system 400 further comprises a device 200, whereby an extension portion 202 of device 200 is shown positioned within at least part of folder 404 and a flange portion 204 of device 200 is positioned within at least part of a sleeve 406 and around hypotube 402 proximally of folder 404. Sleeve 406, as shown in this exemplary embodiment, slidingly engages hypotube 402 and may be moved in a forward or backward direction as indicated by the arrow in the figure. FIG. 6B illustrates an embodiment of system 400 where, instead of having the flange portion 204, the device 200 comprises two or more wings 304. Accordingly, in FIG. 6B, the wings 304 of the device 200 are shown in the collapsed position positioned within at least part of a sleeve 406 and around hypotube 402 proximal to folder 404.

In at least one embodiment, device 200 is an autoexpandable metallic stent mounted over a hypotube 402 as shown in FIGS. 6A and 6B. Device 200 may be compressed by sleeve 406 and folder 404 such that both the extension portion 202 and the flange portion 204 or the wings 304 (as applicable) are in their collapsed positions. In at least one embodiment, at least part of system 400 has a diameter of 7 Fr to 8 Fr (2.3 to 2.7 mm), with an exemplary device 200 having a compressed diameter of about 1.8 to 2.0 mm.

Figure 7A:
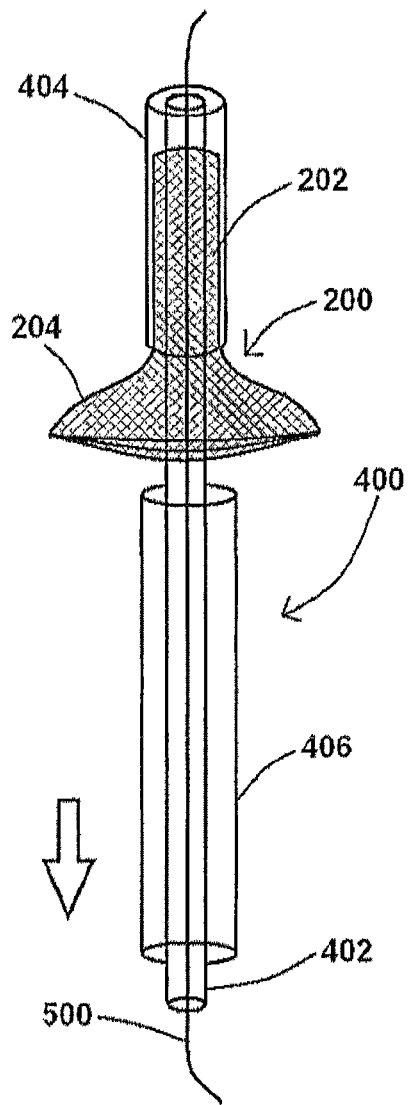
FIGS. 7A and 7B show an exemplary system of the present disclosure with portions thereof being moved to allow for device deployment, according to the present disclosure.
Figure 7B:
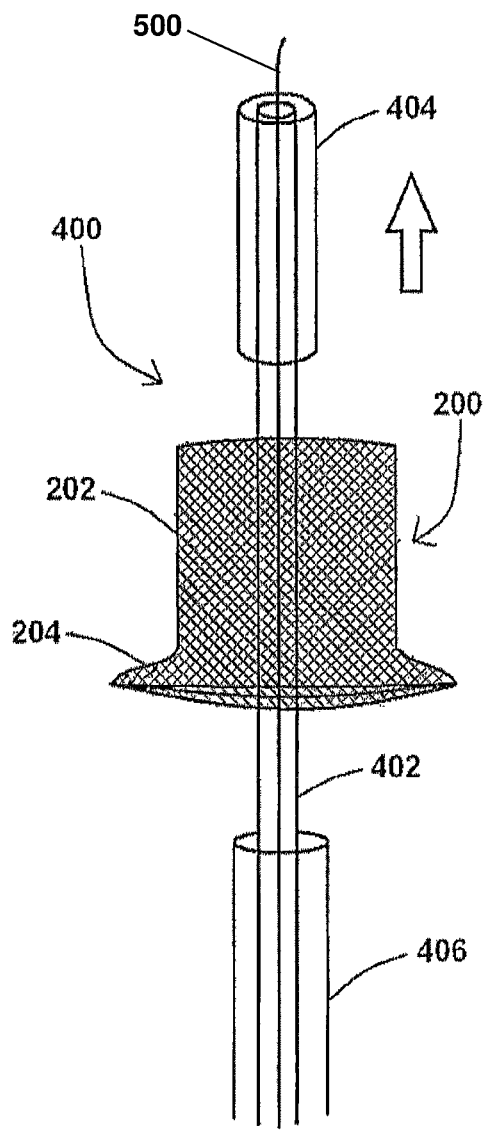

FIGS. 7A and 7B show exemplary embodiments of at least portions of systems for preventing stroke of the present disclosure. While FIGS. 7A and 7B illustrate an embodiment of the device 200 comprising flange portion 204, it will be understood that this disclosure is equally applicable to any embodiment of the device 200 disclosed herein (including, but not limited to, device 200 comprising wings 304).

As shown in FIG. 7A, an exemplary system 400 comprises hypotube 402 to which folder 404 is coupled thereto. System 400, as shown in FIGS. 7A and 7B, further comprises sleeve 406 slidingly engaged around hypotube 402. Device 200 may be positioned at least partially within folder 404 and sleeve 406 prior to deployment, whereby the extension portion 202 of device 200 may be positioned within at least part of folder 404 in a collapsed position, and whereby the proximal portion (i.e. the flange portion 204 or wings 304, as applicable) of device 200 may be positioned within at least part of a sleeve 406 in a collapsed position (as shown in FIGS. 6A and 6B).

As shown in FIG. 7A, device 200 may be partially deployed as follows. First, and in an exemplary method of positioning a stent within a body, a wire 500 (a guide wire, for example) may be advanced within a body at or near a desired location of device 200 deployment. When wire 500 has been advanced, hypotube 402, along with any portions of system 400 coupled to hypotube 402, may be advanced along wire 500 within the body. As shown in FIGS. 7A and 7B, initial advancement of at least a portion of system 400 may comprise advancement of hypotube 402, folder 404, sleeve 406, and device 200 positioned within folder 404 and sleeve 406.

When device 200 has been positioned within a body at or near a desired position, sleeve 406 may be withdrawn toward the proximal end of hypotube 402 (in the direction of the arrow shown in the figure). This step may be performed prior to, during, or after the step of positioning the distal end of hypotube 402 within a vessel (for example, a vessel branching off the aortic arch 104). As sleeve 406 is slid toward the proximal end of hypotube 402, the flange portion 204 of device 200 is allowed to expand as shown in FIG. 7A Likewise, in the at least one embodiment where the device 200 comprises two or more wings 304, sliding the sleeve 406 toward the proximal end of the hypotube 402 results in the wings 304 moving to the expanded position shown in FIGS. 3A-3C. While at this step the flange portion 204/wings 304 are deployed, the extension portion 202 remains within the folder 404. Accordingly, the extension portion 202 remains undeployed and does not yet engage or anchor to an arterial wall.

Further deployment of device 200 within a body is shown in FIG. 7B. As shown in FIG. 7B, and upon movement of folder 404 away from device 200 (in a direction shown by the arrow in the figure, for example), extension portion 202 of device 200 may deploy as shown in FIG. 7B. As folder 404 is moved away from device 200 (by, for example, advancement of hypotube 402 within a body), extension portion 202 of device 200 is no longer positioned within folder 404, thereby permitting expansion/deployment of extension portion 202.

Figure 8A:
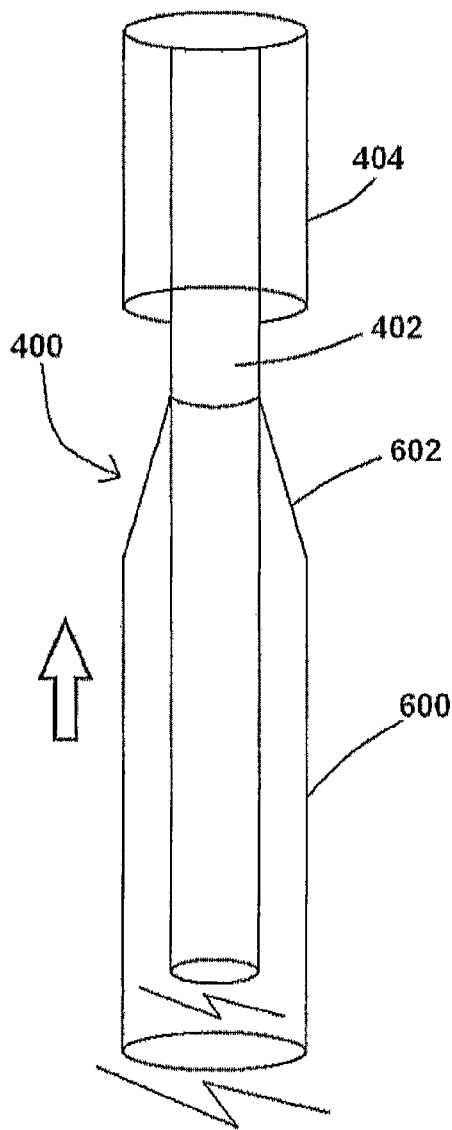
FIGS. 8A and 8B show at least a portion of an exemplary system for preventing stroke, said system comprising a conical dilator useful to facilitate removal of at least a portion of the exemplary system from the body, according to the present disclosure.
Figure 8B:
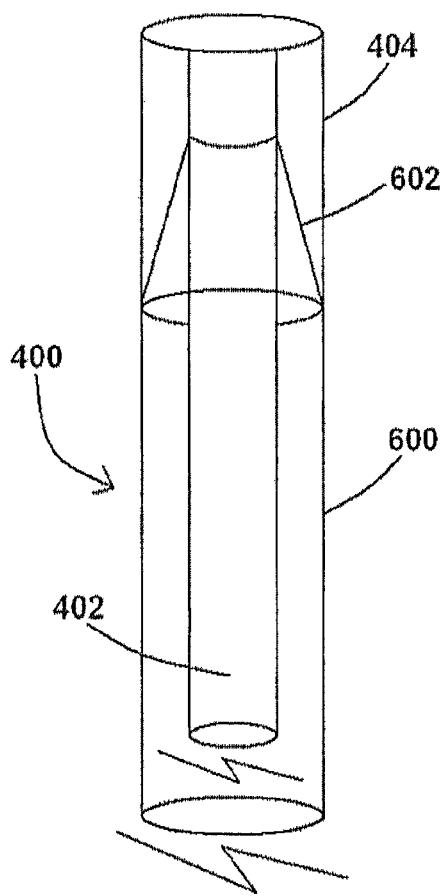

FIGS. 8A and 8B show exemplary embodiments of at least a portion of a system for preventing stroke. In at least one embodiment, system 400 comprises a conical dilator 600 slidingly engaged around a hypotube 402 coupled to a folder 404. As shown in FIG. 8A, an exemplary conical dilator 600 may comprise a tapered distal end 602, wherein the tapered distal end 602 is sized and shaped to engage the inside of folder 404. To engage folder 404, conical dilator 600 may slide along hypotube 402 in a direction indicated by the arrow in FIG. 8A. An exemplary embodiment of the engagement of conical dilator 600 and folder 404 is shown in FIG. 8B.

Engagement of conical dilator 600 with folder 404, as shown in FIGS. 8A and 8B, may facilitate the removal of at least a portion of system 400 from a body after positioning device 200. For example, and as shown in FIGS. 7A and 7B, after deployment of device 200 within a body, the portion of system 400 comprising folder 404 is positioned, for example, further within a vessel than device 200. Removal of the portion of the system 400 comprising hypotube 402 and folder 404 would require, for example, pulling that portion of system 400 back through device 200. As shown in the exemplary embodiments of FIGS. 7A-8B, folder 404 may, for example, become caught on device 200 and/or a portion of a body, preventing effective removal of that portion of system 400.

Figures 9A, 9B:
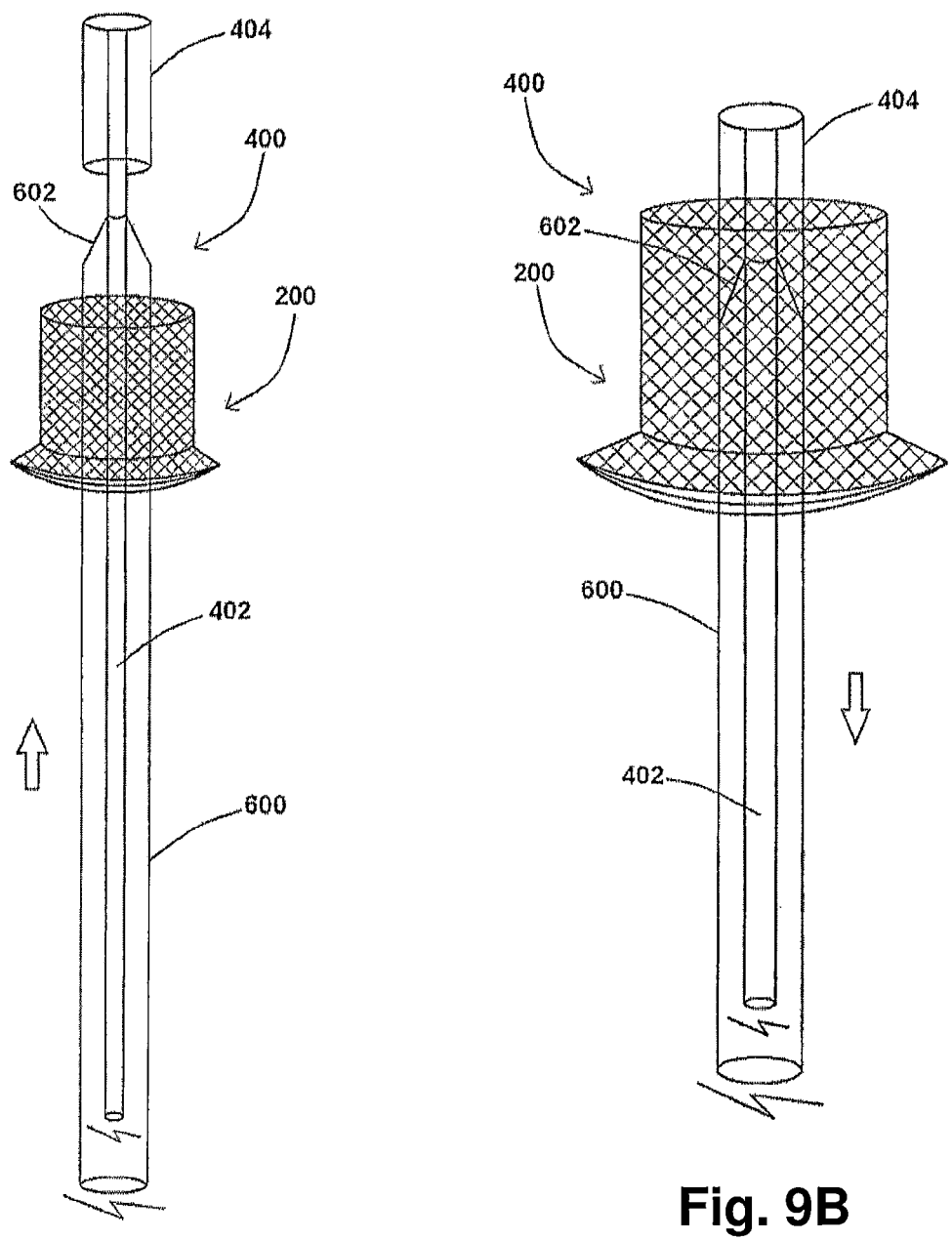
FIGS. 9A and 9B show additional embodiments of an exemplary system for preventing stroke, according to the present disclosure.

In at least one embodiment, and by engaging folder 404 with conical dilator 600, folder 404, along with the portion of system 400 coupled to folder 404, may be removed from a body after placement of a device 200 as shown in FIGS. 9A and 9B. As shown in FIG. 9A, and after a device 200 has been deployed, a user of system 400 may slide a conical dilator 600 along hypotube 402 in a direction indicated by the arrow. Conical dilator 600, in the example shown in FIGS. 9A and 9B, is sized and shaped to fit within the spaces between convex struts 212 of device 200. After conical dilator 600 has engaged folder 404, as shown in FIG. 9B, when hypotube 402 is withdrawn from the body in a direction indicated by the arrow, folder 404 is also removed from the body without becoming caught on device 200.

In at least one embodiment of a system for preventing stroke of the present disclosure, system 400 comprises a device 200, a hypotube 402, and a folder 404 coupled to hypotube 402 at or near the distal end of hypotube 402. Device 200, in at least one embodiment, may be autoexpandable, i.e. device 200 has a "memory" allowing it to expand to a native configuration after being retracted/compressed to fit within, for example, folder 404 and sleeve 406. System 400, in at least one embodiment, may further comprise, or be used in connection with, a femoral catheterization kit known and used in the marketplace.

Figure 14:
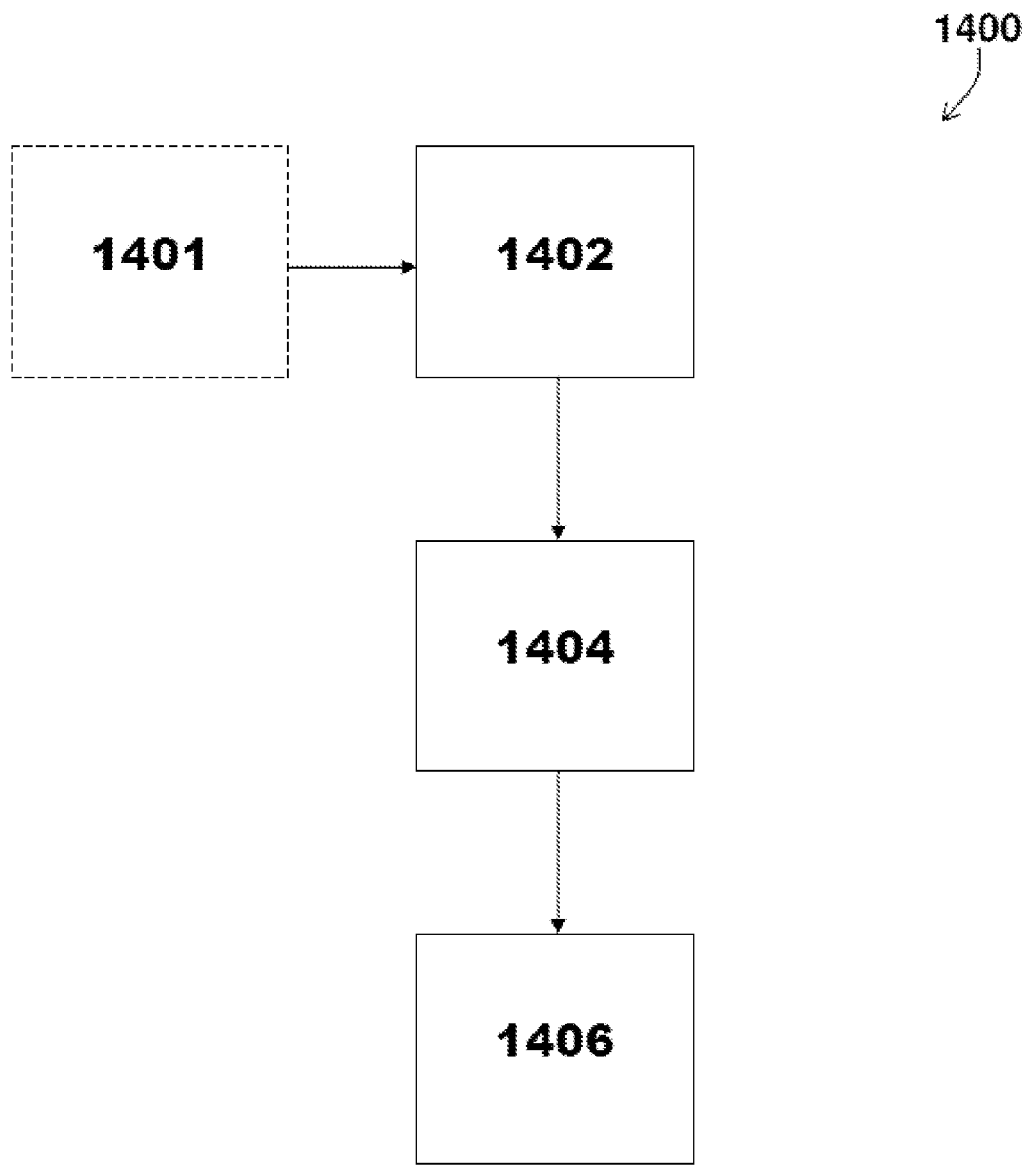
FIG. 14 shows a flow chart of an exemplary method for preventing stroke according to the present disclosure.

Now referring to FIG. 14, at least one method of preventing stroke will now be described using the components of the previously described systems for reference and explanatory purposes. Primarily, at step 1402, the device 200 is positioned within a body. In at least one exemplary embodiment of the present disclosure, the percutaneous placement of the percutaneous carotid emboli rerouting device (device 200) may be performed in an angiography procedure room. Prior to positioning device 200 at step 1402, a user may optionally perform a contrast aortogram, for example, to map out the aortic arch 104 and where the cerebral vessels merge with aortic arch 104 (optional step 1401). For safety, patient preparation and sterile precautions are recommended as for any angioplasty procedure.

In at least one embodiment of the method 1400 for preventing stroke, the optional step 1401 of the method 1400 additionally or alternatively comprises performing a percutaneous angiogram using technique(s) known in the art under local anesthesia. As referenced above, the percutaneous angiogram maps the aortic arch 104 so that a user of a device 200 and/or system 400 of the present disclosure can, for example, select an appropriately-sized device 200 and/or system 400 (or portion(s) thereof) when performing the procedure.

At step 1402, to facilitate positioning the device 200 within a body, a user may introduce a wire 500 (such as guide wire as shown in FIG. 7A) to reach the innominate artery 114 and/or the left common carotid artery 116. After wire 500 has been positioned, portions of system 400 may be mounted over the guide wire 500 and progressed to the level of the entrance of the innominate artery 114 and/or the left common carotid artery 116. Said portions of system 400 may include hypotube 402 and a folder 404 distally mounted thereto, and may further comprise a sleeve 406, wherein an exemplary device 200 may be positioned at least partially within folder 404 and sleeve 406, as shown in FIG. 10A. After the device(s) 200 are properly positioned at step 1402, the method 1400 advances to step 1404 where the device(s) 200 are deployed.

Deployment of device 200 at step 1404, in an exemplary embodiment of a method of the present application for performing the same, is as a follows. Under fluoroscopy, sleeve 406 may be pulled back to allow the delivery of the proximal portion of the stent (the flange portion 204 or wings 304 of device 200) as shown in FIG. 10B. The diameter of flange portion 204 or wings 304 that exceeds the diameter of the innominate artery 114 and/or the left common carotid artery 116 impedes the progression of device 200 within said arteries, thus giving the user/operator time to deliver and anchor the second portion of the stent (the extension portion 202 of device 200) by, for example, forward progression of hypotube 402 as shown in FIGS. 7B and 10C. In addition to preventing the device 200 from progressing within the artery, when the flange portion 204 and/or wings 304 are expanded upon delivery to the artery of interest, such structures also provide support over the aortic wall of the aortic arch 104 at the level of proximal aortic ostium in which the device 200 is deployed.

In at least one embodiment, deployment of the device 200 at step 1404 may be facilitated through the use of radiopaque markers 214. Where the device 200 comprises radiopaque markers 214, prior to anchoring the extension portion 202 of the device 200, such markers 214 can be used to assist with ensuring proper alignment. Specifically, the user/operator can visualize the radiopaque markers 214 through fluoroscopy or other technology and rotate the device 200 accordingly so that the convex struts 212 are positioned as desired relative to the direction of blood flow within the aortic arch 104. In this manner, the radiopaque markers 214 can facilitate placement and orientation of the device 200. In various embodiments, device 200 can be positioned approximately perpendicular to, or in a direction of (i.e. approximately parallel with), or in an oblique manner relative to, blood flow in the aortic arch 104, and can even be positioned/deployed in an oblique manner (not parallel or perpendicular), should such a deployment be desired.

When device 200 has been positioned at step 1402 and deployed at step 1404, the method 1400 may advance to step 1406 where the hypotube 402 and folder 404 are removed from the body, for example, by introducing conical dilator 600 as described herein. In at least one example, the tapered distal end 602 of conical dilator 600 is advanced until it engages folder 404 of hypotube 402, as shown in FIGS. 8A-9B, 10D and 10E, effectively forming a single unit (conical dilator 600+hypotube 402+optionally wire 500 (not shown)). This "unit" may then removed through the convex struts 212 as shown in FIG. 10E, and distally to the femoral artery for which at least part of system 400 was initially introduced.

Now referring to FIGS. 11-13B, an exemplary system 700 for preventing stroke of the present disclosure is shown. At times, temporary placement of the devices 200 disclosed herein may be desired (as opposed to chronic or permanent placement). In such cases, it is necessary to retrieve the device 200 from the patient after a prescribed period of time has elapsed or other indications are observed. System 700 comprises a retrieval system for use in retrieving one or more devices 200 previously positioned within an artery extending from the aortic arch 104.

System 700 comprises a sleeve catheter 702, a retrieval device 704, and at least one device 200. The sleeve catheter 702 is configured for intravascular insertion and advancement, and comprises an open distal end 708, a proximal end 710 (see FIG. 11C), and a lumen 712 extending therebetween. The retrieval device 704 is slidably disposed within the lumen 712 of the sleeve catheter 702 and comprises a proximal end (not shown) for manipulation by a user/operator and a distal end 706 configured for advancement through the open distal end 708 of the sleeve catheter 702. The distal end 706 of the retrieval device 704 further comprises one or more attachment portions 714 positioned thereon, each of which are configured to engage the at least one device 200.

The retrieval device 704 may comprise any configuration suitable for slidably advancing through the lumen 712 and through the open distal end 708 of the sleeve catheter 702. It will be appreciated that the specific configuration of the retrieval device 704 and its one or more attachment portions 714 can be selected and/or adapted to correspond with the configuration of the device(s) 200 to be retrieved. For example, in the embodiments shown in FIGS. 11A-12, the retrieval device 704 is configured to retrieve a device 200 comprising two or more wings 304 and, thus, comprises one or more wires. Alternatively, in the embodiment of FIGS. 13A and 13B, the retrieval device 704 comprises an elongated catheter having one or more attachment portions 714 configured to engage either the wings 304 or the flange portion 204 (as applicable) of the device 200. Furthermore, the proximal portion (the wings 304 or the flange portion 204, as applicable) of the device 200 may be additionally configured to engage or receive the attachment portion(s) 714 of the retrieval device 704.

Now referring back to FIGS. 11A-11C, an embodiment of a system 700 for retrieving at least one device 200 having two or more wings 304 is shown. This embodiment of the system 700 has a retrieval device 704 comprising one or more wires slidably disposed within the lumen 712 of the sleeve catheter 702. Each of the wires of the retrieval device 704 of this embodiment comprises an attachment portion 714 configured to securely grab at least one of the wings 304 of the device 200. For example, an attachment portion 714 may be curved or comprise a hook capable of grabbing one of the wings 304 of the device 200. Alternatively, the attachment portion 714 may comprise a screw shape or any other configuration capable of securely grabbing at least one of the wings 304 of the device 200.

While the number of wires of the retrieval device 704 may correspond with the number of wings 304 present on the device(s) 200 to be retrieved, it will be recognized that the retrieval device 704 may comprise any number of wires. For example, in the event the retrieval device 704 comprises more wires than the number of wings 304 present on the device(s) 200 to be retrieved, more than one wire may be attached to a single wing 304 and/or any extra wires may remain unattached. Conversely, in the event the retrieval device 704 comprises fewer wires than the number of wings 304 present on the device(s) 200 to be retrieved, the available wires may be strategically attached to the wings 304 such that a sufficient amount of force can be exerted on each device 200 to move it to the collapsed position and thus disengage the device 200 from the aortic and arterial walls.

Figure 12:
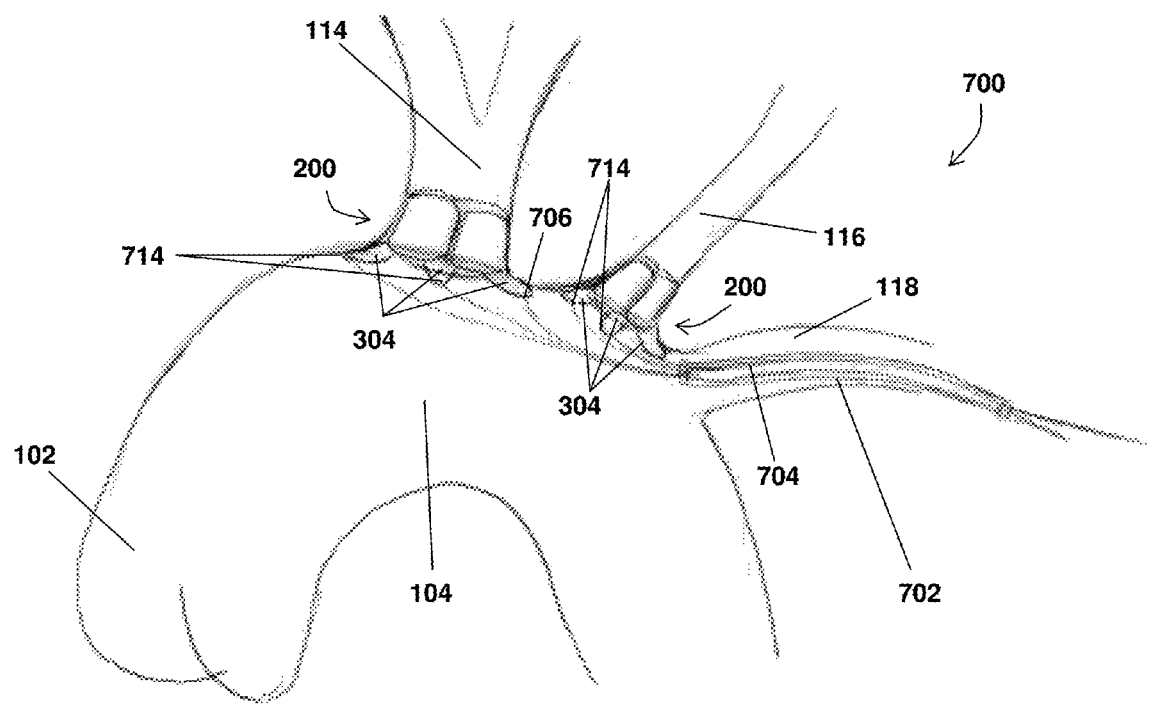
FIG. 12 shows at least a portion of an exemplary system for retrieving two devices previously positioned within arteries extending from a portion of an aorta, according to the present disclosure.

FIG. 12 shows the system 700 as applied to two devices 200 positioned within the innominate artery 114 and the left common carotid artery 116, respectively. In this embodiment, each of the devices 200 comprises three wings 304 and the retrieval device 704 comprises six attachment portions 714 (here, shown as wires). As such, each wire of the retrieval device 704 corresponds with and is attached to one wing 304 of a device 200. It will be appreciated that a user/operator can manipulate the wires as a whole (thus manipulating both devices 200 concurrently) or, alternatively, manipulate the two devices 200 independently by identifying and maneuvering only those select wires that correspond with each independent device 200.

Figure 11A:
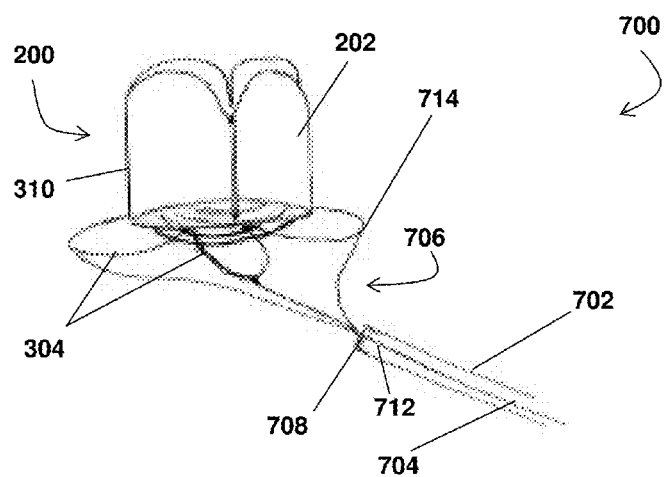
FIGS. 11A-11C show various steps of a method for retrieving a device previously positioned within a body, according to the present disclosure.
Figure 13A:
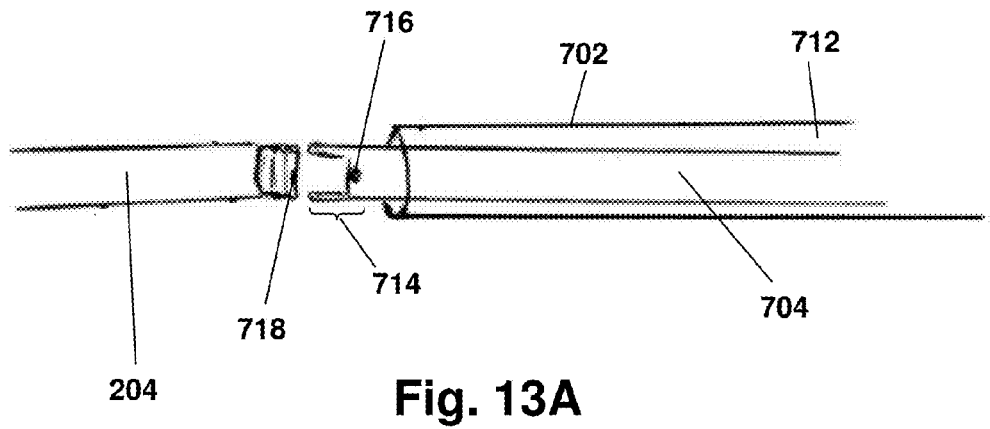
FIGS. 13A and 13B show embodiments of an attachment portion of the exemplary system for retrieving a device previously positioned within a body.
Figure 13B:
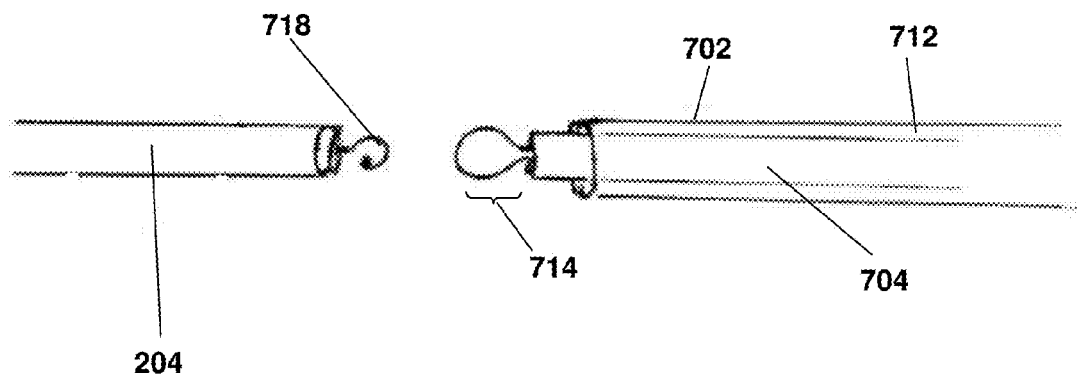

While FIGS. 11A-12 illustrate embodiments of the system 700 comprising a retrieval device 704 having wires, the retrieval device 704 of the system 700 may comprise any configuration suitable for slidably advancing through the lumen 712 and the open, distal end 708 of the sleeve catheter 702. Furthermore, the configuration of the one or more attachment portions 714 of the retrieval device 704 can be selected and/or adapted to correspond with the configuration of the device 200 to be retrieved. FIGS. 13A and 13B show two non-limiting examples of such alternative embodiments of a retrieval device 704. In these embodiments, the retrieval device 704 comprises an elongated catheter having an attachment portion 714 on or near its distal-most end. Likewise, the proximal portion (flange portion 204 or wings 304, as applicable) of the device 200 may be configured to correspond with the attachment portion 714 of the retrieval device 704. For example, in the embodiment shown in FIG. 13A, the attachment portion 714 of the retrieval device 704 defines a cavity having female threads disposed therein and a magnet 716, while the flange portion 204 of the device 200 comprises a corresponding portion 718 having male screw threads and a magnet. Similarly, FIG. 13B shows an embodiment where the attachment portion 714 of the retrieval device 704 comprises a lace and the corresponding portion 718 of the flange portion 204 comprises a corresponding hook tip. Accordingly, in each of the aforementioned embodiments, the device 200 may be easily engaged by the attachment portion 714 of the retrieval device 704.

After the attachment portion 714 of the retrieval device 704 is securely coupled with the device 200 (via the corresponding portion 718 or otherwise), a user/operator can manipulate the proximal end (not shown) of the retrieval device 704 and thus manipulate the device 200. In this manner, a user/operation may move a device 200 positioned within an artery extending from the aortic arch 104 to its collapsed position and, thus, disengage the device 200 from the aortic and arterial walls.

Figure 11B:
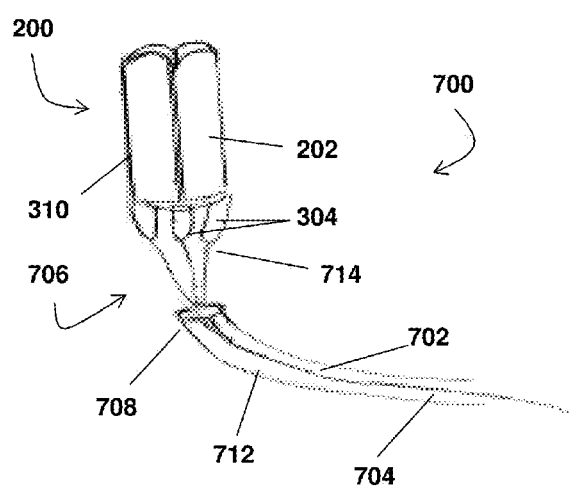
Figure 11C:
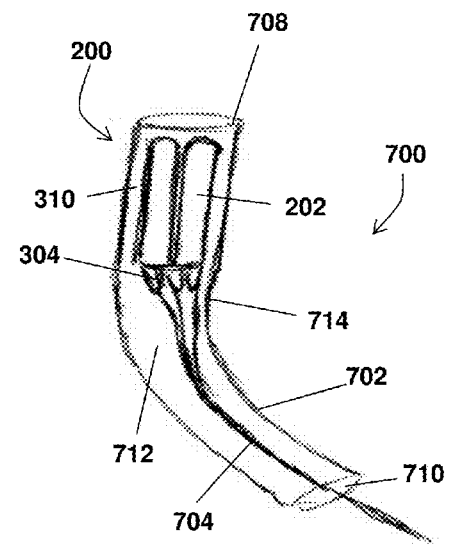

In the embodiments shown in FIGS. 11A-11C, moving the device 200 from the expanded/anchored position to the collapsed/disengaged position is accomplished by pulling the distal end/attachment portion 714 of the retrieval device 704 toward the proximal end 710 of the sleeve catheter 702, thereby applying pressure to the device 200 in the direction of the arrow shown in FIG. 11B. Due to the configuration of the wires of the retrieval device 704, moving the retrieval device 704 in a proximal direction applies pressure to the wings 304 and pulls them from the expanded position to the collapsed position. As the wings 304 are coupled with the extension portion 202 of the device 200, this motion translates to the extension portion 202 as well, thereby causing the entire device 200 to move to a collapsed position and disengage the aortic and arterial walls. After the device 200 is disengaged, the retrieval device 704 (and thus the collapsed device 200) is then slidably removed from the sleeve catheter 702 and the patient's body.

The various devices, systems, and methods for preventing stroke of the present disclosure have various benefits to patients with various diseases and/or disorders of the heart and/or circulatory system. For example, patients with chronic atrial fibrillation (non-valvular atrial fibrillation), recurrence transient ischemic attack, atrial fibrillation and anticoagulation contraindications, and/or left atrial appendage thrombosis may have their risk of stroke either reduced or eliminated by way of an exemplary devices, systems, and/or method of the present disclosure. In addition, patients with acute myocardial infarct with left ventricular thrombus, atrial flutter (ablation and pulmonary vein isolation), cardiomyopathy with left ventricular enlargement, non-obstructive thrombus of a mechanical heart valve, patent foramen ovale (cryptogenic ischemic stroke) and/or an acute infection endocardiatis with valve vegetation without valve insufficiency under medical treatment (vegetation>1 cm which currently oblige to surgical remotion) may also benefit from the present disclosure.

Furthermore, it is noted that the various devices, systems, and methods for preventing stroke of the present disclosure have advantages as compared to anticoagulant and antiplatelet therapies, as not all patients are suitable for such therapies (given the high risk of bleeding, for example), and the relative cost of such therapies, which would be substantially higher as compared to the devices and systems as referenced herein. The various devices and systems would be useful for various aortic arch configurations, noting that there is diversity among arches.

While various embodiments of devices, systems, and methods for the prevention of stroke have been described in considerable detail herein, the embodiments are merely offered by way of non-limiting examples of the disclosure described herein. It will therefore be understood that various changes and modifications may be made, and equivalents may be substituted for elements thereof, without departing from the scope of the disclosure. Indeed, this disclosure is not intended to be exhaustive or to limit the scope of the disclosure.

Further, in describing representative embodiments, the disclosure may have presented a method and/or process as a particular sequence of steps. However, to the extent that the method or process does not rely on the particular order of steps set forth herein, the method or process should not be limited to the particular sequence of steps described. Other sequences of steps may be possible. Therefore, the particular order of the steps disclosed herein should not be construed as limitations of the present disclosure. In addition, disclosure directed to a method and/or process should not be limited to the performance of their steps in the order written. Such sequences may be varied and still remain within the scope of the present disclosure.

The invention claimed is:

1. A stroke prevention system, the stroke prevention system comprising:
    a stroke prevention device comprising:
        an extension portion having a first end and a second end, the extension portion sized and shaped to fit within an artery extending from an aortic arch;
        an anchor portion comprising a plurality of wings coupled with the second end of the extension portion, the anchor portion sized and shaped to prevent the stroke prevention device from advancing into the artery extending from the aortic arch in which the first end of the extension portion may be positioned and each comprising a first attachment portion; and
        two or more parallel convex struts positioned across an opening defined within the second end of the extension portion, the two or more parallel convex struts configured to divert an embolus from entering the artery when the first end of the extension portion is positioned within the artery;
    a sleeve catheter configured for intravascular insertion and advancement, the sleeve catheter comprising a proximal end, an open distal end, and a lumen extending therebetween; and
    a retrieval device slidably disposed within the lumen of the sleeve catheter, the retrieval device comprising a proximal end for manipulation by the user and a distal end comprising one or more attachment portions, each of which are configured to engage the anchor portion of the stroke prevention device; and
    wherein the first attachment portion of the anchor portion of the stroke prevention device is configured to be engaged by the one or more attachment portions of the distal end of the retrieval device, wherein each of the one or more attachment portions of the retrieval device are configured to engage the first attachment portion of the anchor portion of the stroke prevention device to remove the stroke prevention device from the artery.

2. The stroke prevention system of claim 1, wherein the two or more parallel convex struts comprises four or more parallel convex struts.

3. The stroke prevention system of claim 1, wherein the two or more parallel convex struts are positioned between about 0.75 mm to about 1.0 mm, inclusive, from one another.

4. The stroke prevention system of claim 1, wherein when the stroke prevention device is positioned within the artery extending from an aortic arch, the two or more parallel convex struts are positioned approximately perpendicular to, in a direction of (i.e. approximately parallel with), or in an oblique manner relative to, a direction of blood flow within the aortic arch.

5. The stroke prevention system of claim 1, wherein when the stroke prevention device is positioned within the artery extending from an aortic arch, the two or more parallel convex struts are positioned approximately parallel with a direction of blood flow within the aortic arch.

6. The stroke prevention system of claim 1, wherein the diameter of each of the two or more parallel convex struts is between about 0.25 mm to about 1.0 mm, inclusive.

7. The stroke prevention system of claim 1, wherein the anchor portion is autoexpandable from a collapsed configuration to an expanded configuration.

8. The stroke prevention system of claim 1, wherein the stroke prevention device further comprises one or more radiopaque markers positioned upon one or more of the plurality of wings.

9. The stroke prevention system of claim 1, wherein each wing of the plurality of wings comprises a wire forming a loop relative to the second end of the extension portion.

10. The stroke prevention system of claim 1, wherein the extension portion comprises a stent frame without an extension mesh coupled thereto or formed therein.

11. The stroke prevention system of claim 10, wherein the stent frame comprises a plurality of extension struts connected to one another by way of one or more connection struts.

12. A stroke prevention system, the stroke prevention system comprising:
a stroke prevention device comprising:
an extension portion having a first end and a second end, the extension portion sized and shaped to fit within an artery extending from an aortic arch;
an anchor portion comprising a plurality of wings coupled with the second end of the extension portion, the anchor portion sized and shaped to prevent the stroke prevention device from advancing into the artery extending from the aortic arch in which the first end of the extension portion may be positioned and each comprising a first attachment portion; and
two or more parallel convex struts positioned across an opening defined within the second end of the extension portion, the two or more parallel convex struts configured to divert an embolus from entering the artery when the first end of the extension portion is positioned within the artery;
a sleeve catheter configured for intravascular insertion and advancement, the sleeve catheter comprising a proximal end, an open distal end, and a lumen extending therebetween; and
a retrieval device slidably disposed within the lumen of the sleeve catheter, the retrieval device comprising a proximal end for manipulation by the user and a distal end comprising one or more attachment portions, each of which are configured to engage the anchor portion of the stroke prevention device; and
wherein the first attachment portion of the anchor portion of the stroke prevention device is configured to be engaged by the one or more attachment portions of the distal end of the retrieval device, wherein each of the one or more attachment portions of the retrieval device are configured to engage the first attachment portion of the anchor portion of the stroke prevention device to remove the stroke prevention device from the artery;
wherein the anchor portion is autoexpandable from a collapsed configuration to an expanded configuration; and
wherein the stroke prevention device further comprises one or more radiopaque markers positioned upon one or more of the plurality of wings.

13. The stroke prevention system of claim 12, wherein the two or more parallel convex struts comprises four or more parallel convex struts.

14. The stroke prevention device of system 12, wherein the two or more parallel convex struts are positioned between about 0.75 mm to about 1.0 mm, inclusive, from one another.

15. The stroke prevention device of system 12, wherein the extension portion comprises a stent frame without an extension mesh coupled thereto or formed therein.

16. A method for preventing stroke, the method comprising the steps of:
introducing a device for preventing stroke into a body, the device comprising:
an extension portion having a first end and a second end, the extension portion sized and shaped to fit within an artery extending from an aortic arch,
an anchor portion comprising a plurality of wings coupled with the second end of the extension portion, the anchor portion sized and shaped to prevent the device from advancing into the artery extending from the aortic arch in which the first end of the extension portion may be positioned, and
two or more convex struts positioned across an opening defined within the second end of the extension portion, the two or more convex struts configured to divert an embolus from entering the artery when the first end of the extension portion is positioned within the artery;
wherein a first attachment portion of the anchor portion of the device is configured to be engaged by one or more attachment portions of a distal end of a retrieval device, the retrieval device further comprising a proximal end for manipulation by a user, wherein each of the one or more attachment portions of the retrieval device are configured to engage the first attachment portion of the anchor portion of the device to remove the device from the artery;
navigating the device within the body until the device reaches an aortic arch; and
positioning the device within a vessel branching from the aortic arch so that the two or more convex struts are positioned approximately perpendicular to, in a direction of (i.e. approximately parallel with), or in an oblique manner relative to, a direction of blood flow within the aortic arch; and
introducing a retrieval system into the body, the system comprising:
a sleeve catheter configured for intravascular insertion and advancement, the sleeve catheter comprising a proximal end, an open distal end, and a lumen extending therebetween, and
the retrieval device slidably disposed within the lumen of the sleeve catheter, the retrieval device comprising the proximal end for manipulation by the user and the distal end comprising the one or more attachment portions, each of which are configured to engage the anchor portion of the device;
navigating the sleeve catheter within the body until the open distal end of the sleeve catheter reaches an aortic arch;
advancing the distal end of the retrieval device through the open distal end of the sleeve catheter so that the one or more attachment portions engage the anchor portion of the device;
disengaging the engaged device from the first vessel; and
withdrawing the engaged device and the retrieval system from the body.

17. The method of claim 16, wherein the step of positioning the device is performed by aligning the device within the vessel by detecting one or more radiopaque markers positioned upon the device and placement of the device within the vessel does not significantly affect upstream blood flow patterns.

18. The method of claim 16, further comprising the step of:
   anchoring the device within the vessel by deploying the extension portion and the anchor portion of the device.

19. The method of claim 18, wherein the step of anchoring the device within the vessel further comprises moving the extension portion from a collapsed position to an expanded position and moving the anchor portion from a collapsed position to an expanded position.

* * * * *